United States Patent [19]

Nelson et al.

[11] Patent Number: 5,840,873

[45] Date of Patent: *Nov. 24, 1998

[54] LABELED HYBRIDIZATION ASSAY PROBES USEFUL FOR THE DETECTION AND QUANTIFICATION OF MULTIPLE NUCLEIC ACID SEQUENCES

[75] Inventors: Norman Charles Nelson, San Diego, Calif.; James Stuart Woodhead, Raglan; Ian Weeks, Cardiff, both of Great Britain; Azzouz Ben Cheikh, Del Mar, Calif.

[73] Assignee: Gen-Probe Incorporated, San Diego, Calif.

[ * ] Notice: The term of this patent shall not extend beyond the expiration date of Pat. No. 5,756,709 and 5,658,737 and 5,827,656.

[21] Appl. No.: 858,803

[22] Filed: May 19, 1997

Related U.S. Application Data

[63] Continuation of Ser. No. 683,122, Jul. 16, 1996, which is a continuation of Ser. No. 331,107, Oct. 28, 1994, abandoned.

[51] Int. Cl.$^6$ .......................... C07H 21/02; G01N 33/00; C12N 15/00; C09K 3/00
[52] U.S. Cl. ................................ 536/24.3; 436/94; 935/8; 252/700
[58] Field of Search .................................. 435/5, 6, 91.1, 435/91.2, 810; 252/89.1, 700; 436/164, 174, 171, 94; 536/23.1, 24.3, 24.33, 25.3; 935/1, 16, 19, 76, 77

[56] References Cited

U.S. PATENT DOCUMENTS

| | | | |
|---|---|---|---|
| 3,539,574 | 11/1970 | Sheehan et al. | 260/279 |
| 4,238,195 | 12/1980 | Boguslaski et al. | 23/230 B |
| 4,672,028 | 6/1987 | Olson | 435/5 |
| 4,806,463 | 2/1989 | Goodchild et al. | 435/5 |
| 4,918,000 | 4/1990 | Schubert | 435/2 |
| 4,927,769 | 5/1990 | Chang et al. | 436/518 |
| 4,931,223 | 6/1990 | Bronstein et al. | 252/700 |
| 4,946,958 | 8/1990 | Campbell et al. | 546/104 |
| 5,030,557 | 7/1991 | Hogan et al. | 435/6 |
| 5,094,939 | 3/1992 | Okada et al. | 435/6 |
| 5,108,896 | 4/1992 | Philo et al. | 435/7.5 |
| 5,185,439 | 2/1993 | Arnold et al. | 536/24.3 |
| 5,206,179 | 4/1993 | Ramsey | 436/537 |
| 5,216,143 | 6/1993 | Hogan et al. | 536/24.32 |
| 5,283,174 | 2/1994 | Arnold et al. | 435/6 |
| 5,424,413 | 6/1995 | Hogan et al. | 536/24.31 |
| 5,451,503 | 9/1995 | Hogan et al. | 435/6 |
| 5,658,737 | 8/1997 | Nelson et al. | 435/6 |

FOREIGN PATENT DOCUMENTS

| | | | |
|---|---|---|---|
| 0281390 | 3/1988 | European Pat. Off. | C07H 1/06 |
| 0313219 | 9/1988 | European Pat. Off. | C07F 9/24 |
| 0519070 | 12/1992 | European Pat. Off. | |
| 0617288 | 9/1994 | European Pat. Off. | |
| 8803957 | 6/1988 | WIPO . | |
| 8902476 | 3/1989 | WIPO . | |
| 9100511 | 1/1991 | WIPO | G01N 21/76 |
| 9101384 | 2/1991 | WIPO | C12Q 1/68 |
| 9212255 | 7/1992 | WIPO | C12Q 1/00 |
| 9325711 | 6/1993 | WIPO | C12Q 1/68 |
| 9417397 | 4/1994 | WIPO . | |

OTHER PUBLICATIONS

Iitia, et al., Simultaneous detection of two cystic fibrosis alleles using dual–label time–resolved fluorometry. *Mol. and Cell.Probes* 6:505–512 (1992).

Nelson et al., Detection of Acridinium Esters by Chemiluminescence. *Non–Isotopic Probe Techniques* (Academic Press, 1992).

Newman and H. Powell, Synthesis and properties of 4,5–Dimethylacridine and 1,4,5,8–Tetramethylacridine. *J. Org. Chem.*, 26:812–815 (1961).

Seitz, Immunoassay Labels based on Chemiluminescence and Bioluminscence. *Clin. Biochem.* 17:120–126 (1984).

Vuori, et al., Dual–Label Time–Resolved Fluoroimmunoassay for simultaneous detection of myoglobin and carbonic anhydrase III in serum. *Clin. Chem.* 37:2087–2092 (1991).

Weeks, et al., Acridinium Esters as High Specific Activity Labels in Immunoassays. *Clin. Chem.* 29:1474–1478 (1983).

Collins. W. (ed.) *Alternative Immunoassays* (John Wiley & Sons, Ltd.) pp. 103–182 and 203–217 (1985).

Davis, et al., eds., Basic Methods in Molecular Biolgoy, *Elsevier Science Publishing Co., Inc.*, New York, New York, pp. 42–46 (1986).

Kenten, et al., Clinical Chemistry, 38/6, pp. 873–879 (1992).

Lovgren, T., Time–resolved fluoroimmunoassay, advantages and limitations, *Luminescence Immunoassays and Molecular Applications*, pp. 233–253, CRC Press (1990).

Weeks, I., et al., Immunoassay using acridinium esters, *Methods in Enzymology*, Academic Press, Inc., 133:366–387 (1986).

Zomer, G., et al., Chemiluminogenic labels, old and new, Anal. Chem. ACTA, 227:11–19 (1989).

*Primary Examiner*—Bradley L. Sisson
*Attorney, Agent, or Firm*—Charles B. Cappellari; Carlos A. Fisher

[57] ABSTRACT

The invention relates to methods for simultaneously or sequentially detecting multiple nucleic acid analytes in a single medium utilizing oligonucleotide hybridization probes coupled to different chemiluminescent labeling reagents. The methods may be used in a heterogeneous, homogeneous or non-homogeneous assay system. The invention also relates to specific combinations of chemiluminescent labeling reagents suitable, when coupled to an oligonucleotide probe, for use together in methods for the detection of multiple nucleic acid analytes. The invention also concerns kits useful in these methods.

9 Claims, 25 Drawing Sheets

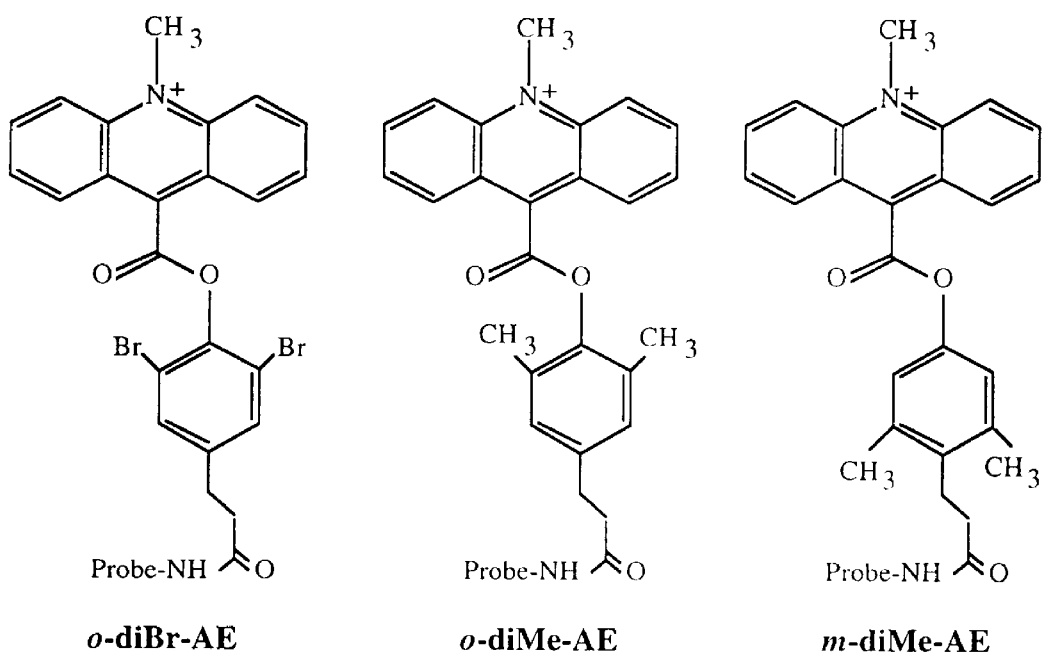
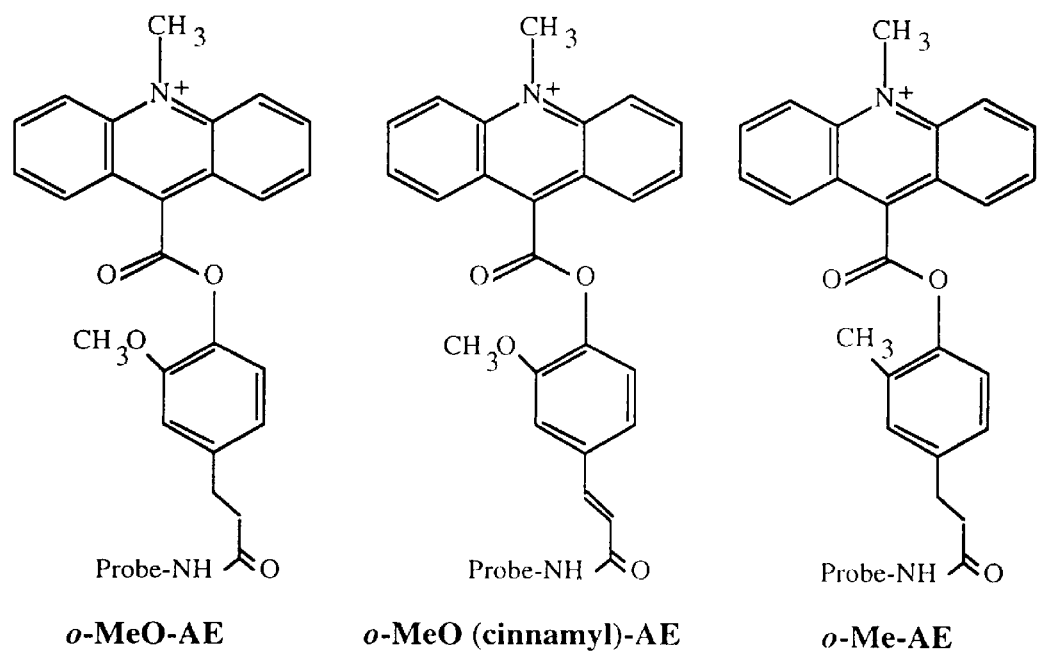
FIG. 1B

Predicted Label Pairs

Selection Criteria:

*Light-off:*
Time-to-peak: 2-fold difference
Duration: 2-fold difference

*Half-life of hydrolysis (unhybridized, coupled):*
HPA: 10-fold difference
DH + Sep: 50-fold difference
Sep: 250-fold difference

| | | Standard .4/3.0 0.67 | naphthyl .32/0.5 .52 | o-diBr .28/.42 4.1 | 1-Me .5/3.0 2.0 | 4,5-diMe .5/1.8 4.2 | 2,7-diMe .5/1.8 5.7 | o-Me 4.0/40 7.3 | o-MeO(c) 0.6/8.0 2.1 | o-MeO .35/0.5 0.92 | o-AE .90/5.0 1.2 | o-F .16/.38 0.92 | 1-Me-o-F .18/.46 3.2 | 1-Me-m-diH .25/.45 2.2 |
|---|---|---|---|---|---|---|---|---|---|---|---|---|---|---|
| Standard .4/3.0 0.67 | 1 | | | | | | | | | | | | | |
| | 2 | | | | | | | | | | | | | |
| | 3 | | | | | | | | | | | | | |
| naphthyl .32/0.5 .52 | 1 | Y | | | | | | | | | | | | |
| | 2 | Y | | | | | | | | | | | | |
| | 3 | Y | | | | | | | | | | | | |
| o-diBr .28/.42 4.1 | 1 | Y | N | | | | | | | | | | | |
| | 2 | Y | N | | | | | | | | | | | |
| | 3 | Y | N | | | | | | | | | | | |
| 1-Me .5/3.0 2.0 | 1 | N | Y | Y | | | | | | | | | | |
| | 2 | N | Y | Y | | | | | | | | | | |
| | 3 | N | Y | Y | | | | | | | | | | |
| 4,5-diMe .5/1.8 4.2 | 1 | N | Y | Y | N | | | | | | | | | |
| | 2 | N | Y | Y | N | | | | | | | | | |
| | 3 | N | Y | Y | N | | | | | | | | | |
| 2,7-diMe .5/1.8 5.7 | 1 | N | N | Y | N | N | | | | | | | | |
| | 2 | Y | Y | Y | N | N | | | | | | | | |
| | 3 | Y | Y | Y | N | N | | | | | | | | |
| o-diMe .25/>80 >30 | 1 | N | N | Y | N | Y | Y | | | | | | | |
| | 2 | Y | Y | Y | Y | Y | Y | | | | | | | |
| | 3 | Y | Y | Y | Y | Y | Y | | | | | | | |

Key: 1 = HPA; 2 = DH + Sep; 3 = Sep
Structures of the AE labels cited above are shown in Figures 1A–1C; here, o-MeO(c) = o-MeO (cinnamyl)

FIG. 2A

Predicted Label Pairs

*Selection Criteria:*

Light-off
Time-to-peak: 2-fold difference
Duration: 2-fold difference

Half-life of hydrolysis (unhybridized, coupled)
HPA: 10-fold difference
DH + Sep: 50-fold difference
Sep: 250-fold difference

| | | Standard .4/3.0 0.67 | naphthyl .32/0.5 .52 | o-diBr .28/.42 4.1 | 1-Me .5/3.0 2.0 | 4,5-diMe .5/1.8 4.2 | 2,7-diMe .5/1.8 5.7 | o-diMe .25/>80 >30 | o-Me 4.0/40 7.3 | o-MeO(c) 0.6/8.0 2.1 | o-MeO .35/0.5 0.92 | o-AE .90/5.0 1.2 | o-F .16/.38 0.92 | 1-Me-o-F .18/.46 3.2 | 1-Me-m-diF .25/.45 2.2 |
|---|---|---|---|---|---|---|---|---|---|---|---|---|---|---|---|
| o-Me 4.0/40 7.3 | 1 | N | N | Y | Y | Y | Y | Y | | | | | | | |
| | 2 | Y | Y | Y | Y | Y | Y | Y | | | | | | | |
| | 3 | Y | Y | Y | Y | Y | Y | Y | | | | | | | |
| o-MeO(c) 0.6/8.0 2.1 | 1 | Y | Y | Y | Y | Y | Y | N | Y | | | | | | |
| | 2 | Y | Y | Y | Y | Y | Y | Y | Y | | | | | | |
| | 3 | Y | Y | Y | Y | Y | Y | Y | Y | | | | | | |
| o-MeO .35/0.5 0.92 | 1 | Y | N | N | N | Y | Y | Y | Y | Y | | | | | |
| | 2 | Y | N | N | Y | Y | Y | Y | Y | Y | | | | | |
| | 3 | Y | N | N | Y | Y | Y | Y | Y | Y | | | | | |
| o-AE .90/5.0 1.2 | 1 | Y | Y | Y | Y | Y | Y | Y | Y | N | Y | | | | |
| | 2 | Y | Y | Y | Y | Y | Y | Y | Y | N | Y | | | | |
| | 3 | Y | Y | Y | Y | Y | Y | Y | Y | N | Y | | | | |
| o-Fl .16/.38 0.92 | 1 | Y | N | N | Y | Y | Y | N | Y | Y | N | Y | | | |
| | 2 | Y | N | N | Y | Y | Y | Y | Y | Y | N | Y | | | |
| | 3 | Y | N | N | Y | Y | Y | Y | Y | Y | N | Y | | | |
| 1-Me-o-F .18/.46 3.2 | 1 | Y | N | N | Y | Y | Y | N | Y | Y | N | Y | N | | |
| | 2 | Y | N | N | Y | Y | Y | Y | Y | Y | N | Y | N | | |
| | 3 | Y | N | N | Y | Y | Y | Y | Y | Y | N | Y | N | | |
| 1-Me-m-diF1 .25/.45 2.2 | 1 | Y | N | N | Y | Y | Y | N | Y | Y | N | Y | N | N | |
| | 2 | Y | N | N | Y | Y | Y | Y | Y | Y | N | Y | N | N | |
| | 3 | Y | N | N | Y | Y | Y | Y | Y | Y | N | Y | N | N | |

Key: 1 = HPA; 2 = DH + Sep; 3 = Sep
Structures of the AE labels cited above are shown in Figures 1A-1C; here, o-MeO(c) = o-MeO (cinnamyl)

FIG. 2B

|   |            | Half-life @ pH 8.5 |
|---|------------|--------------------|
| 1 | diBr       | ~ 2 min            |
| 2 | 2,7-diMe   | ~ 2 min            |
| 5 | o-MeO(cinn)| ~ 1 min            |
| 6 | o-Me       | ~ 4 min            |
| 7 | o-diMe     | very slow          |

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:1:

ATTCCCTACA ATCCCCAAAG TCAA                                            2 4

( 2 ) INFORMATION FOR SEQ ID NO:2:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:2:

AATTTAATAC GACTCACTAT AGGGAGACAA ATGGCAGTAT TCATCCACA          4 9

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:3:

AATTTAATAC GACTCACTAT AGGGAGACCC TTCACCTTTC CAGAG              4 5

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) SEQUENCE DESCRIPTION: SEQ ID NO:4:

GTTTGTATGT CTGTTGCTAT TAT                                            2 3

( 2 ) INFORMATION FOR SEQ ID NO:5:

( i ) SEQUENCE CHARACTERISTICS:
   ( A ) LENGTH: 29 base pairs
   ( B ) TYPE: nucleic acid
   ( C ) STRANDEDNESS: single
   ( D ) TOPOLOGY: linear ( i i ) SEQUENCE DESCRIPTION: SEQ ID NO:5:

CTACTATTCT TTCCCCTGCA CTGTACCCC                29

( 2 ) INFORMATION FOR SEQ ID NO:6:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) SEQUENCE DESCRIPTION: SEQ ID NO:6:

CCAATCCCCC CTTTTCTTTT AAAATTGTGG ATG            33

( 2 ) INFORMATION FOR SEQ ID NO:7:

( i ) SEQUENCE CHARACTERISTICS:
      ( A ) LENGTH: 46 base pairs
      ( B ) TYPE: nucleic acid
      ( C ) STRANDEDNESS: single
      ( D ) TOPOLOGY: linear ( i i ) SEQUENCE DESCRIPTION: SEQ ID NO:7:

AATTTAATAC GACTCACTAT AGGGAGAAGT GACATAGCAG GAACTA    46

( 2 ) INFORMATION FOR SEQ ID NO:8:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) SEQUENCE DESCRIPTION: SEQ ID NO:8:

TGCACCAGGC CAGATGAGAG AACCA                     25

( 2 ) INFORMATION FOR SEQ ID NO:9:

( i ) SEQUENCE CHARACTERISTICS:
      ( A ) LENGTH: 49 base pairs
      ( B ) TYPE: nucleic acid
      ( C ) STRANDEDNESS: single
      ( D ) TOPOLOGY: linear ( i i ) SEQUENCE DESCRIPTION: SEQ ID NO:9:

ATTTTAATAC GACTCACTAT AGGGAGATTG GACCAGCAAG GTTTCTGTC    49

( 2 ) INFORMATION FOR SEQ ID NO:10:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) SEQUENCE DESCRIPTION: SEQ ID NO:10:

AGATTTCTCC TACTGGGATA GGT                       23

( 2 ) INFORMATION FOR SEQ ID NO:11:

( i ) SEQUENCE CHARACTERISTICS:
      ( A ) LENGTH: 31 base pairs

```
        ( B ) TYPE: nucleic acid
        ( C ) STRANDEDNESS: single
        ( D ) TOPOLOGY: linear ( i i ) SEQUENCE DESCRIPTION: SEQ ID NO:11:

GTCATCCATC  CTATTTGTTC  CTGAAGGGTA  C                                        3 1
```

LABELED HYBRIDIZATION ASSAY PROBES USEFUL FOR THE DETECTION AND QUANTIFICATION OF MULTIPLE NUCLEIC ACID SEQUENCES

This application is a continuation application of U.S. Ser. No. 08/683,122, filed Jul. 16, 1996, entitled "Compositions and Methods For The Simultaneous Detection and Quantification Of Multiple Specific Nucleic Acid Sequences", which is a file wrapper continuation application of U.S. Ser. No. 08/331,107, filed Oct. 28, 1994, entitled "Compositions and Methods For The Simultaneous Detection and Quantification Of Multiple Specific Nucleic Acid Sequences", now abandoned.

FIELD OF THE INVENTION

This invention concerns compositions and methods for simultaneously detecting and quantifying multiple nucleic acid analytes in a single sample. Specifically, the present invention involves the use of two or more different chemiluminescent compounds coupled to single-stranded nucleic acid hybridization probes. When each probe has selectively hybridized to its target nucleic acid, the chemiluminescent compound or "label" coupled thereto may be distinguished from the label coupled to unhybridized probe and from a different label hybridized to a different target nucleic acid. Upon initiation of a chemiluminescent reaction, the light emitted is an indication of the presence or amount of each hybridized probe, and thus of the presence or amount of each target nucleic acid. The present invention also discloses methods for separately detecting and/or measuring the light emitted by each chemiluminescent label in a single tube as an indication of the presence and/or quantity of two or more nucleic acid analytes.

BACKGROUND OF THE INVENTION

Light emission as the result of a chemical reaction is known to those skilled in the chemical arts. See Schuster and Schmidt, *Chemiluminescence of Organic Compounds, in Advances in Physical Organic Chemistry* 18: 187–238 (V. Gold & D. Bethel eds., Academic Press 1982). Additionally, the absorbance or diffusion of light at one or more wavelengths has been applied to the quantifying of bacterial cells in suspension (see *Manual of Methods for General Bacteriology* 191 (American Society for Microbiology 1981) for the measurement of nucleic acid and protein concentration in solution, id. at 456 and 359 respectively) and as a means of following the purification of various compounds by chromatography and other purification and separation techniques. However, these latter techniques are generally not specific with regard to the identification of a particular compound, such as a protein or nucleic acid species.

The use of chemiluminescent reagents as labeling reagents in analyte-specific immunological assays is known in the art. See e.g., W. Rudolf Seitz, *Immunoassay Labels based on Chemiluminescence and Bioluminescence, Clin. Chem.* 17:120–126 (1984). The use of acridinium derivatives as specific labeling reagents in such assays has been described in Weeks et al., *Acridinium Esters as High Specific Activity Labels in Immunoassays, Clin. Chem.* 29:1474–1478 (1983).

Assays employing chemiluminescent labels or "reporter groups" proceed according to a generalized mechanism. In this mechanism, the light-emitting compound reacts with a second compound which causes the light-emitting compound to enter a transient high energy state. When the excited molecule subsequently returns to a low energy state, a photon is emitted. The reaction may or may not involve additional cofactors or catalysts to facilitate or accelerate the reaction. In a population of such molecules the emitted light can be measured in a light measuring device called a luminometer. The amount of measured light is proportional to the concentration of reacting luminescent compounds in the test sample.

Thus, when the compound is physically associated with an analyte, the amount of light generated is also proportional to the amount of analyte in the sample, so long as any excess or unassociated chemiluminescent reagent has been removed from the sample before reaction and measurement. The compound can be directly bonded to the analyte or can be linked or bonded with a compound which itself is capable of physically associating with the analyte. An example of the latter would be where the chemiluminescent reagent is bonded to an antibody specific for the analyte of interest or to a single-stranded nucleic acid complementary to a nucleic acid whose presence in the test sample is suspected.

Various assay systems for the measurement of more than one specific analyte in a single test sample have been described. In Gorski et al., *J. Histochem. and Cytochem.* 25:881–887 (1977) a single label, acridine orange, was used as a fluorescent vital dye in mixed lymphocyte cultures. After staining the cultures were monitored at two different wavelengths. Because the dye, which intercalates between the bases of nucleic acids, will emit light in the green region if associated with DNA and in the red region if associated with RNA, it is possible to simultaneously measure total cellular DNA and RNA by monitoring these two wavelength regions.

Various assay systems have been devised employing two or more different radioisotopes each incorporated in one of a binding pair, such as a member of an antibody-antigen pair, a receptor-substrate pair or one of two complementary nucleic acid strands. By using radionuclides emitting different kinds of energy (such as $\gamma$ radiation and $\beta$ particle emission) or energies of different intensities it is possible to differentiate between the two radionuclides, and thus between the compounds into which they are incorporated. Scintillation and gamma counters are commercially available which can measure radioactive decay in more than one channel simultaneously.

Thus, in a multi-analyte competition radioimmunoassay (RIA) two or more populations of analyte molecules are labeled with different radioisotopes at a known specific activity (mCi of radioisotope/mmole of analyte). When a test sample is mixed with the labeled analytes, the unlabeled analyte in the test sample will compete with the labeled analyte for binding to an unlabeled specific binding partner. The amount of unlabeled analyte in the test sample is proportional to the decrease in signal as compared to the amount measured without addition of the test sample.

Radioactive assays have obvious disadvantages. Non-radioactive methods for detecting and measuring an analyte in a test sample are known in the art. For example, enzyme-linked immunoassays utilizing biotin and avidin, carbohydrates and lectins have been described, as have assay systems using fluorescent reporter groups such as fluorescein and rhodamine, as well as chemiluminescent reporter groups. Some of these systems also are inherently limited in the sensitivity with which they may detect the analyte of interest due to inherent sensitivity of the label, and/or by the spectral or kinetic characteristics of the particular fluorescent or chemiluminescent compound.

Simultaneous assays of multiple analytes using fluorescent reporter groups having high quantum yields is made more difficult due to the relatively broad spectra and high backgrounds associated with these reagents.

Non-radioactive multiple labeling systems have been reported for the measurement of proteins; Vuori et al., *Clin. Chem.* 37:2087–2092 (1991), and nucleic acids; Iitia et al., *Mol. and Cell. Probes* 6:505–512 (1992), in which chelates of fluorescent lanthanides (e.g., europium, samarium and terbium) are coupled to one of a specific binding pair. The unknown components are assayed either through a competition immunoassay or by nucleic acid hybridization, and the fluorescence is measured. The fluorescent lanthanides have narrow emission peaks and the components of the pairs $Eu^{3+}/Sm^{3+}$ and $Eu^{3+}/Tb^{3+}$ have emission maxima sufficiently far apart that they may be distinguished from each other. Moreover, the post-excitation fluorescent decay of Eu is relatively long lived, while that of Sm and Tb is extremely short, which provides another way of distinguishing the signals: by measuring the fluorescence of each chelate at different times.

A generalized multiple analyte assay system using acridinium ester derivatives as the reporting group was described in Woodhead et al., PCT Application WO91/00511, which is not admitted to be prior art and which enjoys common ownership with the present application. Khalil et al., PCT Application WO92/12255, describe a solid phase dual analyte immunoassay system employing an acridinium or phenanthridinium derivative as a first chemiluminescent reagent, and a 1,2-dioxetane, which is converted to a chemiluminescent reaction intermediate by alkaline phosphatase or β-galactosidase, as a second chemiluminescent reagent. The acridinium derivative yields a short-lived photon signal upon reaction with a triggering solution such as $H_2O_2$. The dioxetane yields a longer-lived signal when triggered by addition of the appropriate enzyme. Each of these reagents can be bonded to one of a specific binding pair and is used in a solid phase sandwich immunoassay. Each signal is measured over a different time period.

SUMMARY OF THE INVENTION

The present invention features the simultaneous detection and quantification of more than one specific nucleic acid sequence in a sample. Specifically, each of the labeling reagents of the present invention is linked to a specific oligonucleotide hybridization assay probe, the labeled probes are mixed and are allowed to hybridize to any nucleic acid contained in the test sample having a sequence sufficiently complementary to the probe sequence to allow hybridization under appropriately selective conditions. A reagent can then be added to the solution which will specifically alter the labeling reagent associated with unhybridized labeled probe while leaving the labeling reagent associated with the hybridized probes substantially unaltered. This allows each labeling compound to be differentially resistant to loss of chemiluminescent potential depending on whether the label is associated with a hybridized or unhybridized probe. In a preferred embodiment, the hybridized probe-associated label is so protected.

Usually, but not necessarily, the reaction of at least two chemiluminescent reagents is initiated simultaneously, and the resulting light emitted by each chemiluminescent reagent is detected and measured essentially simultaneously. However in some modes of the present invention, for example in the multiple pH mode discussed below, the detection and measurement of one or more chemiluminescent reagent is a separate temporal event from the detection and measurement of one or more other chemiluminescent reagents.

The emitted light may be measured differently depending on the multiple analyte detection mode desired. Thus, the light may be detected and measured: 1) at two or more different wavelengths, 2) during a predetermined time period, 3) over more than one set of reaction conditions (such as different concentrations of hydrogen ion), or 4) in a combination of these methods. Depending on the mode and the specific chemiluminescent reagents chosen, the data obtained from this light measurement enables the separate detection and measurement of each chemiluminescent label in the test sample as an indication of the amount of each analyte present therein.

An important feature of the present invention is therefore the design and selection of pairs or sets of chemiluminescent reagents that are capable of emitting signals sufficiently distinct from each other or under sufficiently different conditions to be separately detected and measured upon the occurrence of one or more reaction-triggering events. Equally importantly, the members of each pair or set of reagents of the present invention are similarly susceptible to loss of their chemiluminescent reactivity and similarly resistant to said loss depending on whether coupled to hybridized or unhybridized probe. By virtue of these latter properties, the labeling reagents of the present invention are particularly useful in, although not limited to, a homogeneous assay system in which the presence and quantification of the analytes of interest may be detected and measured without the need for the analyte-bound label to be physically separated from the unbound label prior to detection.

However, Applicant contemplates that the compositions and methods of the present invention may be used in heterogeneous systems or in combinations of homogeneous and heterogenous assay systems as well. By way of illustration only, and not as a limitation on the scope of the present invention, such a system can involve performing a different hydrolysis of unhybridized probe preferentially binding the labeled hybrid (comprising a labeled single-stranded oligonucleotide probe and an unlabeled target nucleic acid) and not the unhybridized labeled oligonucleotide probe to a solid support such as a polycationic microsphere, separating hybridized, from unhybridized probe, and then measuring the chemiluminescence of the hybrid-associated label, either while still bound to the support or after eluting from the support. Methods for differentially hydrolyzing acridinium ester labels coupled to unhybridized probe over the same compound coupled to a hybridized probe are described in Arnold et al., U.S. Pat. No. 5,283,174, which enjoys common ownership with the present invention and is hereby incorporated by reference herein.

Thus, the method and compositions of the present invention make use of the combination of the two properties mentioned above: the ability of each member of a set of labeling compounds to emit a separately distinguishable signal (distinguishability), and the ability of each member of a set to be susceptible to loss of chemiluminescent activity or protected from such loss depending on whether the label is coupled to hybridized or unhybridized probe (selectivity). Both of these properties depend not only on the structure of the labeling compounds themselves but also on the molecular environment in which they are placed during the course of the assay. Additional factors can thus include, without limitation, the type and location of attachment of the label to the nucleic acid probe, the composition of the assay solution, the nature and reactivity of nearby chemical moieties, the steric properties of the labeling compound, and any changes in molecular configuration or conformation of the bound label relative to the nucleic acid probe upon hybridization of the probe to its target nucleic acid.

The exemplary labeling reagents described herein are acridinium derivatives capable of emitting light when reacted with a triggering reagent, for example an alkaline solution of hydrogen peroxide. However, the Applicant contemplates that other chemiluminescent labels or methods (e.g. electrochemiluminescence) and triggering reagents may be used in the multiple analyte assay of the present disclosure, such compounds and methods being apparent to one of ordinary skill in the art in light of the disclosure of this application. Accordingly, the following examples are supplied to fully and clearly describe the best mode of the present invention known to the Applicant at this time and are not intended in any way to limit the scope of the invention.

It is an object of the present invention to provide a rapid, cost-effective and simple method for simultaneously detecting two or more distinct nucleic acid sequences in a test sample wherein the assay may be conducted in a single assay tube.

It is another object of the present invention to provide a rapid, non-radioactive assay for simultaneously quantifying more than one different nucleic acid sequence in a test sample, wherein at least two chemiluminescent labeling compounds are coupled to different oligonucleotide hybridization probes each capable of hybridizing to at least one of such sequences. After hybridizing, the bound chemiluminescent labels are reacted, causing them to emit light which is measured in a luminometer. The wavelengths or reaction kinetics of light emission for each of the labeling compounds are sufficiently unique to allow the separate measurement of the amount of each labeling reagent in the test sample. A luminometer may measure emitted light over a range of wavelengths as a single event, or may independently measure each of several narrow wavelength ranges simultaneously. Examples of the latter are known to those of skill in the art. For example, use may be made of two or more photomultiplier tubes (PMT's), each measuring a different wavelength or range of wavelengths, to simultaneously measure the same sample, or of a diode array detector capable of measuring more than one wavelength of emitted light simultaneously.

It is another object of the present invention to provide a method for the selection of sets of different labeling compounds capable of being coupled to oligonucleotide probes wherein each compound is similarly susceptible to loss of chemiluminescent potential depending on whether associated with a hybridized or unhybridized probe.

It is another object of the present invention to provide a rapid assay method for the detection of the presence of more than one species of organism in a test sample.

It is another object of the present invention to provide a sensitive assay system to detect or quantify the presence of more than one type of nucleic acid in a sample containing small numbers of each type of nucleic acid molecule.

It is another object to provide chemiluminescent labeling reagents suitable for use in a multiple analyte nucleic acid hybridization assay system wherein each such reagent is sufficiently stable until reaction with a triggering reagent to be capable of use in a quantitative assay for the presence of multiple analytes.

It is another object of the present invention to provide chemiluminescent labeling reagents having sufficiently different reaction kinetics to allow differentiation of the signals of each reaction and separate measurement of these signals. By way of example, the "light-off" characteristics of one member of a two member set may cause virtually all the chemiluminescence to be emitted quickly after the triggering reagent is mixed with the bound label. The other member of the set may have "light-off" characteristics which involve a relatively long period of light emission following addition of the triggering reagent. By measuring chemiluminescence at various times after addition of the triggering reagent and performing an analysis of the light emitted during this period, the signals can be effectively differentiated and separately measured.

It is another object of the present invention to provide chemiluminescent labeling reagents which emit light upon "light-off" at sufficiently narrow and different wavelengths that, by choosing the appropriate wavelength ranges for measurement, the signals may be sufficiently differentiated to distinguish one bound labeling reagent from one or more other bound labeling reagents, even when measured simultaneously.

It is another object of the present invention to provide chemiluminescent reagents designed for use as reporter groups, each such reagent attached to a different oligonucleotide hybridization probe capable of specifically hybridizing to a target nucleic acid having a sequence sufficiently complementary thereto to allow detection of the target nucleic acid under hybridization conditions. A feature of the preferred chemiluminescent reagents and assay method is that, when the oligonucleotide hybridization probe to which each such reagent is attached hybridizes to its target nucleic acid, each of the reagents of the present invention is similarly protected from degradation under conditions which will degrade that population of the reagents attached to unhybridized oligonucleotide probe. An additional feature of the chemiluminescent reagents of the present invention is that they are similarly susceptible to degradation when coupled to unhybridized probes. Yet another feature of the preferred method is that, although the labels are protected from degradation when associated with a double-stranded nucleic acid region, each such label is similarly susceptible to reaction with an appropriate triggering reagent causing initiation of a chemiluminescent reaction.

It is another object of the present invention to provide a method for the detection and quantification of more than one analyte in a sample in a single analysis vessel by conducting the chemiluminescent reaction at different pH values by using acridinium ester derivatives which have different pH optima for the chemiluminescent reaction. This is accomplished by labelling one member of an analyte:probe binding pair with a first acridinium ester and labelling members of one or more other analyte:probe binding pairs with one or more other acridinium esters. After allowing the respective members to bind to their analyte pair, if present, the unbound labels are selectively hydrolyzed to destroy the chemiluminescent potential of the acridinium ester coupled thereto. The remaining acridinium ester, coupled to probe:analyte complexes, is then "lighted off" at a first pH, and the light emission characteristics of the resulting reaction are measured over time. The pH is adjusted to a different pH value, and the light emission characteristics again measured over time. This method is not limited to the use of two pH values: it will be readily apparent that three or more chemiluminescent compounds may be used that have different pH optima for the chemiluminescent reaction. Moreover, this method may be used in combination with other discrimination methods described herein, such as by measuring the emitted light at different wavelengths or observation of the reaction kinetics, employing differences in wavelength or reaction kinetics to measure or detect the presence of more than one analyte at each pH increment.

BRIEF DESCRIPTION OF THE DRAWINGS

FIGS. 1A, 1B through 1C show the structures of representative acridinium ester derivatives used as preferred embodiments of labeling reagents in the present invention. For the structure of 1- or 3-me-AE, 1- or 3-me-o-F-AE, and 1- or 3-me-m-diF-AE, a methyl group is shown near the 2 position of the acridinium ring; this indicates that the methyl group may be attached at either the 1 or 3 position.

FIGS. 2A and 2B comprise a chart representing predicted pairs of acridinium ester derivatives which may be used together in the multiple analyte assay of the present invention. A "Y" indicates that two reagents are predicted to be compatible pairs in the invention, and an "N" indicates that the two compounds would be predicted to be incompatible in this assay. The numbers 1 through 3 in the left-hand column of the chart indicate the type of assay system: 1 represents a homogeneous single-phase assay system HPA, 2 indicates differential hydrolysis in the aqueous phase and physical separation of hybridized oligonucleotide probe:target complexes (DH+Sep), 3 indicates an assay system in which no differential hydrolysis takes place, and in which hybridized probe:target complexes are physically separated (Sep). The numbers separated by a slash below each named acridinium ester derivative are the time-to-peak and reaction duration, respectively. The numbers below this line are the half-life of hydrolysis of each labeling reagent while coupled to an unhybridized oligonucleotide probe. Finally, the selection criteria upon which this chart is based is shown at the top of the Figure.

FIG. 3A shows the emitted light of such a reaction mixture containing standard AE only. FIG. 3B shows the emitted light in a reaction containing o-F-AE alone. FIG. 3C shows the emitted light in a reaction mixture containing both standard AE and o-F-AE.

FIGS. 9A and 9B show the separate spectra of 2, 7 o-diMe-AE and standard AE, respectively. FIG. 9C shows a computer-generated superimposition of each spectrum in a single plot. FIG. 9D shows the computer-generated simulation of the two spectra.

DETAILED DESCRIPTION OF THE PREFERRED EMBODIMENTS

Figure 1A:
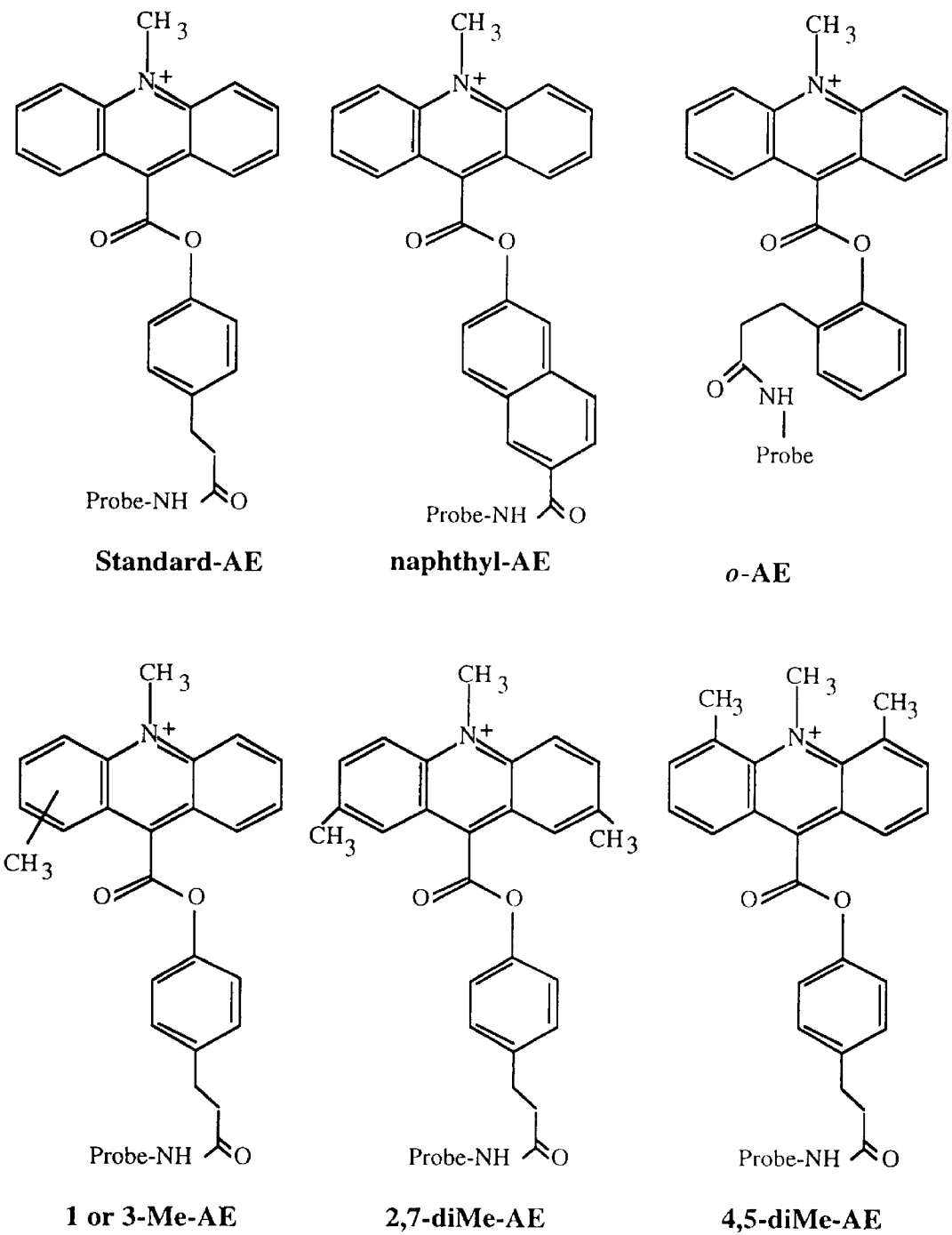

The present invention comprises compositions and methods for the specific detection of multiple different analytes, preferably nucleic acids, in a single test sample. Thus, in a preferred embodiment, the invention can be used to detect the presence of more than a single nucleic acid sequence in a test or clinical sample. In a particularly preferred embodiment, such nucleic acid sequence may indicate a particular disease state or infection.

Definitions

Unless expressly indicated otherwise, the following terms have the following meanings in the present application.

By a "nucleic acid analyte" is meant at least one nucleic acid or nucleotide sequence region the presence and/or amount of which is sought to be detected with a single labeling reagent by the methods and compositions of the present invention when present in a sample. The analyte may be a single nucleic acid molecule having one or more distinct target regions, or more than one different molecule each one of which has one or more distinct target regions. Alternatively, an analyte may be a particular nucleotide sequence contained within a single nucleic acid; hence, a single nucleic acid may contain more than one nucleic acid analyte. However, the Applicant contemplates that it may sometimes be desirable that more than one target region, whether on the same or different nucleic acid molecules, or both, be detected using the same probe label. This would allow, for example, both chromosomal r-DNA and ribosomal RNA of a first organism to be targeted with one or more probes bearing one label, and the chromosomal r-DNA and ribosomal RNA of a second organism to be targeted by one or more probes bearing another label. In such a case the first analyte consists of all the targeted nucleotide sequence regions of the nucleic acid(s) of the first organism, and the second analyte consists of all the targeted nucleotide sequence regions of the nucleic acid(s) of the second organism.

By "target region" or "target nucleotide sequence" is meant the portion of an analyte molecule which binds to a given probe or class of probes. When the analyte is one or more nucleic acid molecules, the target region has a nucleotide sequence in a region of at least one of said nucleic acids which will specifically bind a oligonucleotide hybridization probe under hybridization conditions which do not favor the hybridization of said probes to nontargeted nucleic acids or nucleotide sequence regions. A particular target region may be completely separate from other target regions, whether contained on the same or different nucleic acid molecules. Alternatively, a given target region may, without limitation, be contained on the same nucleic acid molecule as another target region and overlap the other target region by one or more nucleotides, be overlapped by the other target region by one or more nucleotides, or may be contained completely within another target nucleotide sequence.

By "probe", "nucleic acid probe", "hybridization probe", or "oligonucleotide probe" is meant an oligonucleotide having a nucleotide sequence sufficiently complementary to a target nucleotide sequence comprised in a nucleic acid analyte to permit said oligonucleotide to hybridize therewith under highly stringent hybridization conditions. When the word "probe" is used, it will be understood by those of skill in the art that the term applies to one or more oligonucleotide molecules, either identical or non-identical, which are designed, selected, and/or otherwise able to specifically hybridize to a target nucleic acid region. Additionally, a probe as defined herein may comprise a collection of different oligonucleotide molecules targeted to one or more target regions of the same nucleic acid analyte. Thus, the term "probe" as used herein may mean either the singular or the plural, such meaning being made clear by the context of usage in the present specification. By definition, this term preferentially applies to oligonucleotides between 10 and 100 nucleotides in length.

By "untargeted nucleic acids" is meant nucleic acids which are not sought to be detected in a given assay using the methods or compositions of the present invention.

By "sample" or "test sample" is meant any aqueous or water- miscible solution, suspension, or emulsion suspected of containing one or more nucleic acid analytes. Such a sample may include, without limitation, purified or unpurified nucleic acids, virus particles, and/or plant, animal, protozoan or bacterial cells, and may be derived, without limitation, from laboratory, environmental, agricultural, food, human, animal, excretory or secretory sources. A test sample may be produced as the result of a pre-treatment of a previous sample, such as, without limitation, by homogenizing, concentrating, suspending, extracting, solubilizing, digesting, lysing, diluting or grinding the previous sample to put the suspected nucleic acid analyte, if present, in a water-containing environment.

By "chemiluminescent label" is meant any chemical entity or compound, capable of being coupled to another chemical entity or compound, which can participate in a chemically-mediated reaction that results in the emission of light by way of a high energy chemical intermediate. The preferred chemiluminescent labels of the present invention are acridinium derivatives; most preferably acridimium ester derivatives.

By "coupled" is meant that two or more chemical entities or compounds are joined by way of a chemical bond or association. Thus, the term is meant to encompass covalent bonds as well as strong non-convalent bonds such as those formed between avidin and biotin, or a chelating agent and one or more complexed ion.

By "targeted" is meant that a specific chemical, physical, or biological entity is sought to be identified. As so defined, a chemical entity may include a portion of a larger entity, such as a nucleotide sequence region of a nucleic acid. A biological entity under this definition may include a grouping of organisms, such as one or more species, genus, class, family, and so forth.

By a "light-emitting reaction" is meant a triggerable chemical reaction that results in the detectable production of light by one or more of the reactants. Triggerable is intended to mean that the chemical reaction is initiated by the addition of a reactant or energy (such as an electrical charge) to the reaction mixture, or that the reaction kinetics are made more favorable by adjustment of one or more of the reaction conditions, such as temperature or pH.

By "sufficiently distinct" is meant that the wavelength(s) of light emission, time-to-peak, reaction duration or other reaction characteristics of two or more different chemiluminescent labels can be distinguished when they are combined in a reaction mixture and caused to emit light in a triggerable light-emitting reaction.

By "specifically hybridize" is meant that a single-stranded nucleic acid can form a stable hydrogen-bonded duplex with a targeted nucleic acid or nucleotide sequence region under hybridization conditions which do not favor the formation of stable double-stranded duplexes between the same single-stranded nucleic acid and non-targeted nucleic acids or nucleotide sequence regions.

By "similarly protected" is meant that the rates of loss of chemiluminescent potential of different chemiluminescent labels coupled to oligonucleotide hybridization assay probes are decreased depending on whether the probe is hybridized to a targeted nucleic acid or nucleotide sequence region, and that the rates of said loss are preferably within a factor of up to about 250 of each other under the same conditions.

By "similarly susceptable" is meant that the rates of loss of chemiluminescent potential of different chemiluminescent labels coupled to oligonucleotide hybridization assay probes by exposure to a destablizing agent are within a factor of about 50 of each other under identical conditions.

By "chemiluminescent potential" is meant the ability of a given chemiluminescent label to react in a triggerable light-emitting reaction. Loss of chemiluminescent potential occurs when such a chemiluminescent label is chemically degraded or transformed into a non-chemiluminescent compound.

By "reaction pH optimum" or "reaction pH optima" is meant the pH value at which a chemiluminescent reaction involving a given chemiluminescent label will proceed with the highest emission of light under defined conditions. If more than one chemiluminescent compound is present in the same reaction mixture there may be two or more pH optima for the chemiluminescent reaction mixture. The yield of light emission (as a function of pH) may rise steeply as the optimum pH is approached, so that a given chemiluminescent label may emit little light at a first pH while the same label may emit much more light at a pH value 1.0 to 0.5 pH unit different from the first.

By "initiation" is meant the addition of energy, a catalyst or one or more reactant to a reaction mixture containing chemiluminescent reagents which will cause a light-emitting reaction to commence.

By "acridinium derivative" is meant any of the family of chemiluminescent compounds based on the acridinium ring.

By "acridinium ester derivative" is meant any of the family of chemiluminescent compounds based on the acridinium ring and having an ester linkage from the C-9 position.

By "reaction kinetics" is meant the rate of a light-emitting reaction, as determined by the amount of light emitted by the chemiluminescent compound or compounds participating therein in a given time interval, as a function of time. The term "reaction kinetics" is thus intended to include reference to the amount of time between initiation of a chemiluminescent reaction and the maximum extent of light emission (time-to-peak), as well as the duration of light emission following initiation in a given reaction mixture. The reaction kinetics of a reaction mixture containing a given chemiluminescent label can be plotted as amount of light emitted in a given time period versus time, and the curve thus obtained is reproducible and characteristic for a given chemiluminescent reactant under the same reaction conditions.

Figure 1C:
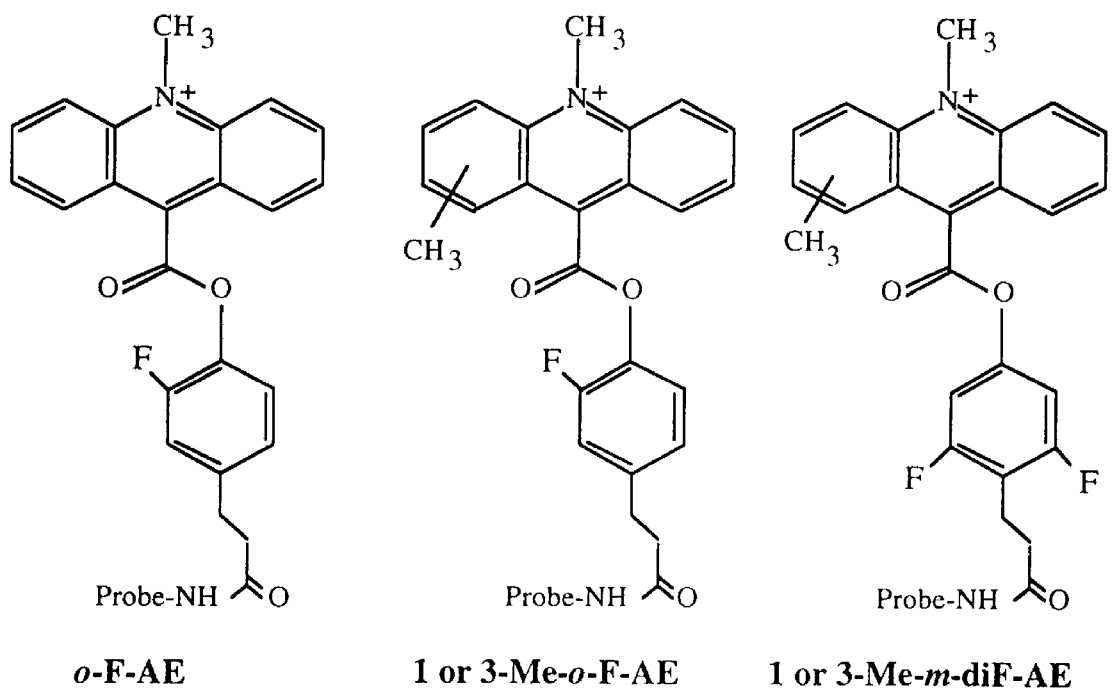

The reagents used in the preferred embodiments of the present invention are acridinium derivatives, preferably acridinium phenyl ester derivatives. FIGS. 1A, 1B and 1C show examples of representative acridinium phenyl ester derivatives. It will be understood that other suitable chemiluminescent reagents and acridinium ester derivatives including other acridinium derivatives may be found suitable for use in the present invention in light of the present disclosure by routine screening. Acridinium phenyl ester compounds are derivatives of acridine possessing a quaternary nitrogen center and derivatized at the 9 position to yield a phenyl ester moiety. Acridinium derivatives useful in the present invention, whether phenyl esters or not, share the property of reacting with hydrogen peroxide to form a transient dioxetan ring involving the C-9 carbon of the acridinium ring, followed by the formation of an excited acridone. The radiative relaxation of the excited acridone results in the production of light. The synthesis of acridinium esters, as well as a general description of their use as chemiluminescent labeling reagents, is described in Weeks et al., *Acridinium Esters as High Specific Activity Labels in Immunoassays, Clin. Chem.* 29:1474–1478 (1984), previously cited and now incorporated by reference herein.

In a preferred embodiment, acridinium esters may be attached, using standard chemical techniques, to a non-nucleotide monomeric unit having a primary amine "linker arm" available for bonding to the acridinium ester moiety which is inserted between contiguous sequences of nucleotides during the chemical synthesis of the oligonucleotides, or placed at a terminal position of the oligonucleotide. See, Arnold, et al., Non-Nucleotide Linking Reagents for Nucleotide Probes, EPO Publication No. EPO 313219 which enjoys common ownership with the present invention, and is now incorporated by reference herein. Thus, the linker arm moiety to which the label will be attached is placed at a predetermined position within the oligonucleotide. It may be placed as an insertion between or as a substitution for one or more nucleotides comprising a nucleic acid sequence sufficiently complementary to at least a portion of a target nucleic acid to be able to hybridize thereto under stringent hybridization conditions. The solid-phase synthesis of oligonucleotides is well known in the art and is described in Brown & Brown, *Modern Machine-Aided Methods of Oligodeoxyribonucleotide Synthesis in Oligonucleotides and Analogues-A Practiced Approach* (1991).

Acridinium ester derivatives may be joined to the linker arm:hybridization probe conjugate using techniques well known in the art. Preferably, Applicants use the methods described in Nelson et al., *Detection of Acridinium Esters by Chemiluminescence* in *Non-Isotopic Probe Techniques* (Academic Press 1992), Arnold et al., *Non-Nucleotide Linking Reagents for Nucleotide Probes*, EPO Publication No. EPO 313219, previously incorporated by reference herein.

Thus, in one such preferred method, an N-hydroxysuccinimide (NHS) ester of acridinium (e.g., 4-(2-succinimidyloxycarbonyl ethyl) phenyl-10-methylacridinium 9-carboxylate fluorosulfonate) is synthesized as described by Weeks et al., supra, previously incorporated by reference. Reaction of the primary amine of the linker arm:hybridization probe conjugate with the selected NHS-acridinium ester is performed as follows. The oligonucleotide hybridization probe:linker arm conjugate synthesized as described above is vacuum-dried in a Savant Speed-Vac™ drying apparatus, then dissolved in 8 μl of 0.125M HEPES buffer (pH 8.0) in 50% (v/v) DMSO. To this solution is added 2 μl of 25 mM of the desired NHS-acridinium ester. The solution is mixed and incubated at 37° C. for 20 minutes.

An additional 3 μl of 25 mM NHS-acridinium ester in DMSO is added to the solution and mixed gently, then 2 μl of 0.1M HEPES buffer (pH 8.0) is added, mixed, and the tube is allowed to incubate for an additional 20 minutes at 37° C. The reaction is quenched with the addition of 5 μl 0.125M lysine in 0.1M HEPES buffer (pH 8.0) in DMSO, which is mixed gently into the solution.

The labeled oligonucleotide is recovered from solution by the addition of 30 μl 3M sodium acetate buffer (pH 5.0), 245 μl water, and 5 μl of 40 mg/ml glycogen. Six hundred forty microliters of chilled 100% ethanol is added to the tube, and the tube is held on dry ice for 5 to 10 minutes. The precipitated labeled nucleic acids are sedimented in a refrigerated microcentrifuge at 15,000 rpm using a standard rotor head. The supernatant is aspirated off, and the pellet is redissolved in 20 μl 0.1M sodium acetate (pH 5.0) containing 0.1% (w/v) sodium dodecyl sulfate (SDS).

The labeled oligomer may then be purified as necessary and desired; methods for the purification of labeled oligonucleotides are well known in the art. In a preferred method described in Arnold, et al., *Acridinium Ester Labeling and Purification of Nucleotide Probes*, U.S. Pat. No. 5,185,439 (which enjoys common ownership with the present application and is incorporated by reference herein), the oligomer is purified using reverse-phase high performance liquid chromatography (RP-HPLC). The sample is applied to a Vydac C4 reverse-phase HPLC column and eluted with a linear gradient from 10% to 15% Buffer B in 25 minutes where Buffer A is 0.1% (w/v) triethylammonium acetate (pH 7.0) in HPLC grade water, and Buffer B is 100% acetonitrile. The absorbance of the resulting effluent is monitored at 260 nm, and 0.5 ml fractions are collected. The fractions are then assayed for chemiluminescence, the fractions corresponding to the major active peak precipitated with ethanol, and the labeled probes resuspended in 0.1M sodium acetate (pH 5.0) containing 0.1% SDS.

The compositions and methods of the present invention are preferably used in conjunction with the hybridization protection assay (HPA) described in Nelson et al., *Detection of Acridinium Esters by Chemiluminescence* in *Non-Isotopic Probe Techniques* (Academic Press 1992) and Arnold et al., U.S. Pat. No. 5,283,174, incorporated by reference herein. In this assay format, the acridinium ester labeling reagents are susceptable to hydrolysis when bound to unhybridized probe but are protected from hydrolysis when bound to hybridized probe. The differential hydrolysis characteristics of this system allow for a homogeneous, single-phase assay wherein hybridization of probe to target, discrimination between hybridized and unhybridized probe, and detection and/or quantification of the labeled hybridized probe can be conducted in a single test tube. However, differential hydrolysis is not the only method whereby hybridized and unhybridized probe can be differentiated; other chemical modifications of the chemiluminescent label, such as adduct formation can or may be able to differentiate between chemiluminescent label coupled to hybridized versus unhy-

EXAMPLE 1

Initial Testing and Screening of Various Acridinium Ester Derivatives

Synthesis of AE Labeling Reagents

N-hydroxysuccinimide (NHS) ester labeling reagents of acridinium ester (AE) derivatives were synthesized generally as described in Weeks et al., supra, previously incorporated by reference. For these syntheses, materials and reagents of highest purity available commercially were obtained from Aldrich, Lancaster Synthesis and Fisher Scientific. 9-Acridinecarboxylic acid (ACA), or a methyl or dimethyl substituted derivative prepared as described below, was converted to the corresponding acridine acid chlorides by refluxing for 4 hours in thionyl chloride. Commercially available hydroxyphenyl- or hydroxynaphthyl acids—namely, 3-(4-hydroxyphenyl)propionic acid, 3-(4-hydroxy-3-methoxyphenyl)propionic acid, 4-hydroxy-3-methoxycinnamic acid, and 6-hydroxy-2-naphthoic acid—were converted to benzyl (Bz) esters by treating their potassium salts with benzyl bromide in 95% ethanol (EtOH) solution under refluxing conditions for about 3 hours. These benzyl esters were then allowed to react with the acridine acid chlorides in anhydrous pyridine for about 4 hours at room temperature to give the acridine esters. The benzyl ester protecting groups were hydrolyzed by treating the acridine esters with 30 wt. % hydrogen bromide (HBr) in acetic acid (HOAc) for about 4 hours at 60° C. The resulting acid was converted to the N-hydroxysuccinimide (NHS) ester reagent using dicyclohexylcarbodiimide (DCC) catalysis in anhydrous tetrahydrofuran (THF). Finally, transformation to the methyl acridinium labeling reagent was accomplished by methylation of the acridine by treatment with excess methyl trifluoromethanesulfonate (methyltriflate) in anhydrous methylene chloride for 5 to 24 hours at room temperature. The NHS-ester labeling reagents used for the standard-AE, naphthyl-AE, o-MeO-AE and o-MeO-(cinnamyl)-AE were prepared in this way. The NHS-ester labeling reagents used for 4,5-diMe-AE, 2,7-diMe-AE, and the mixture of 1- and 3-Me-AE, required synthesis of methyl and dimethyl substituted ACA's as described below.

The 4,5- and 2,7-dimethyl substituted derivatives of 9-acridinecarboxylic acid (ACA) were prepared through the reactions of oxalyl chloride with dimethyl substituted diphenylamines to provide isatin intermediates, followed by rearrangement to produce the corresponding substituted acridines essentially as described for 4,5-dimethylacridine-9-carboxylic acid by M. S. Newman and W. H. Powell, *J. Org. Chem.*, 26 (1961): 812–815. First, 2,2'-dimethyldiphenylamine and 4,4'-dimethyldiphenylamine were prepared by reacting 2 - or 4-methylformanilide with a slight excess of 2- or 4-bromotoluene, respectively, in the presence of anhydrous sodium carbonate and traces of copper in nitrobenzene at 200° C. for 24 hours. Hydrolysis of the resulting N,N-diphenylformamides was accomplished by refluxing them in a 1:1 (v/v) mixture of concentrated HCl in acetic acid (HOAc) for 5 hours to provide the dimethyl-diphenyl amines in good yields after purification over silica. Preparation of the dimethyl substituted acridinecarboxylic acids via isatins then proceeded by reacting the 2,2'-dimethyldiphenylamine or 4,4'-dimethyldiphenylamine prepared above with oxalyl chloride in refluxing carbon disulfide for about 3 hours. After evaporation of the solvent and excess reagents, the yellow residue was taken up into fresh carbon disulfide and treated with aluminum chloride over a period of about 30 minutes, refluxed for 4 hours and set aside at room temperature overnight. Following evaporation of solvents, the residue was partitioned between methylene chloride and cold 10% (v/v) concentrated HCl. The orange isatins were recovered in the organic layer. Finally, treatment of the isatins with 10% (w/v) potassium hydroxide (KOH) for 12 hours under refluxing resulted in formation of 4,5-dimethylacridine-9-carboxylic acid (4,5-diMe-ACA) and 2,7-dimethylacridine-9-carboxylic acid (2,7-diMe-ACA), respectively. In a similar manner, 3-methyldiphenylamine was treated with oxalyl chloride and aluminum chloride to afford a mixture of methylphenylisatins which, after rearrangement by treatment with KOH, as described above, yielded a mixture of 1- and 3-methylacridine-9-carboxylic acid (1- and 3-Me-ACA). Esterification of 4,5-diMe-ACA, 2,7-diMe-ACA, or the mixture of 1- and 3-Me-ACA with the benzyl ester of 3-(4-hydroxyphenyl)propionate and the subsequent reactions described above afforded the NHS ester labeling reagents used for 4,5-diMe-AE, 2,7-diMe-AE, or the mixture of 1- and 3-Me-AE, respectively.

Several substituted hydroxyphenylpropionic acid derivatives, not available commercially, were prepared by conventional methods. 3-(4-Hydroxy-3,5-dibromophenyl) propionic acid was prepared by bromination of 3-(4-hydroxyphenyl)propionic acid with bromine in glacial acetic acid (HOAc). 3-(2-Hydroxyphenyl)propionic acid was prepared by hydrogenation of 2-hydroxycinnamic acid over palladium-on-carbon in absolute ethanol (EtOH). Acridinium ester (AE) preparation could then proceed by coupling ACA with the benzyl esters of these acids as indicated above to provide the NHS-ester labeling reagents used for o-diBr-AE and ortho-AE, respectively.

Additionally, the propionitrile derivatives of several substituted phenols—namely, 2-methylphenol, 2,6-dimethylphenol, 3,5-dimethylphenol, 2-fluorophenol, and 3,5-difluorophenol—were prepared by cyanoethylation via aluminum chloride catalyzed condensation of acrylonitrile with the phenol and isolation of the corresponding substituted 4-hydroxyphenylpropionitrile. These hydroxyphenyl-propionitrile derivatives were then reacted with the acridine acid chlorides and the resulting ester compounds were treated with hydrogen chloride to hydrolyze the nitriles to corresponding propionic acid derivatives which could be processed further as described above to afford the corresponding AE-NHS ester labeling reagents. Alternatively, the propionitriles could be first hydrolyzed to the corresponding propionic acid derivative and synthesis could proceed via the benzyl ester. The final steps to produce the AE-NHS reagents were the same as indicated above. The NHS-ester labeling reagents used for o-diMe-AE, m-diMe-AE, o-Me-AE, o-F-AE, 1- or 3-Me-o-F-AE, and 1- or 3-Me-m-diF-AE were prepared in this manner.

It will be clear to those of skill in the art that these synthesis schemes may be utilized more generally to make additional and different acridinium ester deriviatives for characterization and screening as disclosed below.

Characterization and Screening of AE Derivatives

The chemiluminescence and hydrolysis characteristics of these derivatives were compared to those of standard AE (4-(2-succinimidyloxycarbonyl ethyl) phenyl-10-methylacridinium 9-carboxylate fluorosulfonate).

Exemplary AE derivatives used to demonstrate the present invention were naphthyl-AE, o-diBr-AE, a mixture of 1- and 3-Me-AE, 4,5-diMe-AE, 2,7-diMe-AE, o-diMe-AE, o-Me-AE, m-diMe-AE, o-MeO(cinnamyl)-AE, o-MeO-AE, o-AE (an acridinium ester derivative having the nucleic acid-coupling linker arm attached to the phenyl ring at the ortho position), o-F-AE, a mixture of 1- and 3-Me-o-F-AE, standard AE, and a mixture of 1- and 3-Me-m-diF-AE (see FIG. 1). 1-Me-AE, 1-Me-o-F-AE, and 1-Me-m-diF-AE were only present in a mixture with their 3-methyl isomers; as used in this application, these nomenclatures will be understood to mean a mixture of the corresponding 1- and 3-methyl derivatives. As shown in FIGS. 1A, 1B and 1C, these compounds were used to label various oligonucleotides to be used as hybridization probes. It will be understood by those of skill in the art that the present invention does not depend on the use of any particular probe-target combination. Thus, to choose two or more mutually exclusive probe-target combinations for use with the presently disclosed assay would be routine in light of the present disclosure.

The oligonucleotides were synthesized to contain phosphodiester bonds using standard solid-phase phosphoramidite chemistry using a Biosearch 8750 or ABI 380A DNA synthesizer, and purified using polyacrylamide gel electrophoresis; oligonucleotide synthesis and gel purification techniques are well known in the art (see e.g., Sambrook et al., supra, previously incorporated by reference). Various non-naturally-occurring oligonucleotides, such as those having modified inter-nucleotide linkages such as phosphorothioate linkages or those having sugar or base modifications, are also known in the art and may have advantages such as increased stability in certain applications; these nucleic acid analogs are also contemplated to be used as part of the invention of the present application.

As previously referred to, a linker arm terminating in a primary amine was incorporated into each oligonucleotide's structure at a predetermined position in the nucleotide sequence of the oligonucleotide, thus constituting an insertion between nucleotides in the sequence. See e.g., Arnold et al., *Non-Nucleotide Linking Reagents for Nucleotide Probes*, supra, previously incorporated by reference herein. The AE derivatives were linked to the oligonucleotide via the primary amine of the linker arm, also as detailed above. The labeled probes were characterized and compared with regard to their chemiluminescent, hybridization, and differential hydrolysis properties.

Ten microliter aliquots of the labeled probes were transferred to 12×75 polystyrene tubes, and chemiluminescence was measured in a LEADER® 50 luminometer(Gen-Probe Incorporated, San Diego, Calif.) by the automatic injection of a solution of 200 μl of 0.1% $H_2O_2$ and 0.4N HCl, a 0.1 to 2 second delay, automatic injection of 200 μl of 1N NaOH, and measurement of the chemiluminescence for 5 seconds. The final pH is approximately 13.

The particular luminometer described herein measures light between wavelengths 300 to 650 nm; it will be understood that a luminometer need not detect emitted light in this range of wavelengths in order to be useful in the methods and compositions of the present invention. In fact, in certain modes of the present method, for example, in a multiple wavelength mode, it may be useful or necessary for a luminometer to measure emitted light over a broader or narrower range of wavelengths than is herein described, or over more than one more narrow wavelength independently and simultaneously. Thus, the breadth of wavelengths monitored in the example described herein should be understood as being exemplary and is not a limitation on the scope of the present invention.

The chemiluminescent reaction characteristics were determined by measuring the light emitted by the reacting acridinium ester derivatives. The emitted light was quantified by the luminometer using relative light units (RLU), a unit of measurement indicating the relative number of photons emitted by the sample at a given wavelength or band of wavelengths. The light was detected at multiple time points during the 5 second measurement period. From these data the length of time required for each labeled oligonucleotide to reach peak light emission ("time-to-peak"), and the duration of the light emission, were determined. "Duration" was arbitrarily defined to mean the time required for the RLU to reach 10% of baseline after the peak emission had occurred. These data are presented in Table 1 below.

TABLE 1

LIGHT-OFF CHARACTERISTICS

| Compound | Standard Conditions | | Optimal Conditions | | |
| --- | --- | --- | --- | --- | --- |
| | Peak | Duration | pH | Peak | Duration |
| Std-AE | 0.4s | 3.0s | 11.9 | 0.75s | >5s |
| Naphthyl-AE | 0.32s | 0.5s | 10.2 | 0.5s | >5s |
| o-diBr-AE | 0.28s | 0.42 | 10.2 | 0.5 | >5s |
| 1-Me-AE | 0.5s | 3.0s | 11.9 | 0.75s | >5s |
| 4,5-diMe-AE | 0.5s | 1.8s | 11.9 | 1.0s | >5s |
| 2,7-diMe-AE | 0.5s | 1.8s | 11.9 | 1.3s | >5s |
| o-diMe-AE | 0.25s | >80s | 13.0 | 0.25s | >80s |
| o-Me-AE | 4.0s | 40s | 13.0 | 0.25s | 3.0s |
| m-diMe-AE | 0.36s | 2.3s | nd | nd | nd |
| o-MeO(cinnamyl)AE | 0.6s | 8.0s | 13.0 | 0.5s | 3.8s |
| o-MeO-AE | 0.35s | 0.5s | 11.9 | 0.5s | >0.8s |
| o-AE | 0.9s | 5.0s | 13.0 | 0.5s | >5s |
| o-F-AE | 0.16s | 0.38s | 11.2 | 0.6s | 1.2s |
| 1-Me-o-F-AE | 0.18s | 0.46s | 12.0 | 0.6s | 1.2s |
| 1-Me-m-diF-AE | 0.25s | 0.45s | 11.3 | nd | nd |

Additionally, the pH required for each labeled probe to emit the maximum amount of light was also determined and defined as the "optimal pH". In this determination, the reaction was initiated as described above except that the first reaction solution contained 0.1N HCl rather than 0.4N HCl, and rather than using NaOH, the second reaction solution was 0.24M sodium borate buffer titrated to various pH values. The "time-to-peak" and duration were calculated for each labeled probe at the optimum pH. These data are also found in Table 1.

After determining the chemiluminescent reaction kinetics of the labeled oligonucleotides, the hybridization and hydrolysis characteristics of each oligonucleotide were investigated. The AE hydrolysis characteristics for each hybridized and unhybridized labeled oligonucleotide were determined at a range of temperatures and pH values as described in Nelson et al., supra, previously incorporated by reference herein and as briefly summarized here in the following examples.

EXAMPLE 2

Determination of Hydrolysis Characteristics of Acridinium Ester Derivatives

This example demonstrates a preferred method for screening individual chemiluminescent labels to determine their hydrolysis characteristics, such as the rate of hydrolysis, when coupled to hybridization assay probes. In particular, the method is useful for a preliminary determination of the suitability of one or more acridinium ester derivatives for use in a multiple analyte assay system. Although this method illustrates a preferred method of chemically distinguishing hybridized from unhybridized labeled oligonucleotide probes, other methods of chemically or physically separating single-stranded from wholly or partially double-stranded nucleic acids, such as hydroxyapatite adsorption, gel filtration, or reverse-phase chromatography are well known to those of skill in the art.

General Procedure for Measuring Hydrolysis of Free Probe

Generally, each candidate acridinium ester is coupled to a single-stranded oligonucleotide hybridization assay probe and the probe:AE ester purified, as described above. Ten microliters of each acridinium ester-labeled probe dissolved in PSB (10 mM lithium succinate (pH 5.2), 0.1% lithium lauryl sulfate) were added to a 12×75 mm polystyrene test tube. Multiple replicate tubes are made for each labeled probe to be tested; Applicants usually use 13 replicate tubes for each labeled tube, three of which are used as "time zero" ($T_0$) controls. The $T_0$ controls are placed in a test tube rack at room temperature. To each of these tubes is added 200 µl 0.4N HCl and 0.1% (v/v) $H_2O_2$, followed by addition of 100 µl of Hydrolysis Buffer (0.13–0.19M $Na_2B_4O_7$ (pH 7.6–9.5) and 2–5% (v/v) polyoxyethylene ether (sold under the trade name TRITON® X-100 by Sigma Chemical Co., St. Louis, Mo.). Applicants have found the order of addition at this step to be important. Reagent blanks (negative controls) contain 10 µl of PSB alone and are then treated as are the $T_0$ controls.

One hundred microliters of Hydrolysis Buffer are given to each of the 10 remaining replicates a test tube rack, and the rack is shaken to mix. The test tube rack is immediately placed in a circulating water bath at 60° C. (or any other desired test temperature) and timing is initiated.

At desired time points (for example 1, 2, 4, 7, 10, 20, 30, 40, and 50 minutes), 200 µl of a solution of 0.4N HCl, 0.1% (v/v) $H_2O_2$ are added to one tube from each set and the tube is immediately removed from the water bath to room temperature and mixed. The tube is allowed to stand at room temperature for at least 1 minute.

The chemiluminescence of each sample is measured in a luminometer, by a single injection of a solution containing 1N NaOH, and measurement of the chemiluminescence for 5 seconds. The average RLU's of the negative controls are subtracted from the experimental RLU's. The net RLU's for each sample can then be divided by the average $T_0$ RLU's and multiplied by 100; this yields the %$T_0$ values; the data can be plotted with log (%$T_0$) as the y-axis and time as the x-axis.

Differential Hydrolysis (DH) Ratio Determination

The following is a generalized procedure for measuring the ratio of the hydrolysis of the chemiluminescent label coupled to a hybridized oligonucleotide probe as compared to the hydrolysis of the same label coupled in the same manner to the same probe unhybridized to its target nucleic acid.

Hybridization of the labeled single-stranded oligonucleotide probe is accomplished as follows. The following reagents are combined in a 1.5 ml microcentrifuge tube for each acridinium ester labeled probe to be tested: 15 µl of a solution of PSB containing 0.05–0.1 pmol of the AE-labeled probe (a calculated total RLU potential of about 4–5×10⁶), 0.5–1.0 pmol equivalents of the target nucleotide sequence (e.g., 0.25–0.5 pmol of a nucleic acid having two copies of the target nucleotide sequence), and 5–10 pmoles each of any desired helper probes to facilitate hybridization of the probe to the target nucleic acid. Helper probes, also called helper oligonucleotides, are unlabeled oligonucleotides used to increase the rate to hybridization by disrupting the secondary structure of the target nucleic acid in the area of the target nucleotide sequence, (see Hogan et al., U.S. Pat. No. 5,030,557, which enjoys common ownership with the present application and is incorporated by reference herein). However, the use of helper probes is not essential to the operation of the present invention.

The microcentrifuge tube is also given 15 µl of 2×Hybridization Buffer (200 mM lithium succinate (pH 5.2), 17% (w/v) lithium lauryl sulfate, 3 mM EDTA (ethylenediamine tetraacetic acid) and 3 mM EGTA ([ethylenebis(oxyethylenitrilo)]-tetraacetic acid)). The tube is incubated at a temperature at least about 5° C. below the Tm of the probe:target duplex for at least 30 minutes, then 270 µl of 1×Hybridization Buffer is added. Separate tubes should be made up for each chemiluminescent label:probe combination; one tube from each set (labeled "Hybrid") should contain the labeled probe, the target nucleic acid, and the reagents, another tube (labeled "Control") should be made up using the same probe and reagents without the target nucleic acid. Finally, for each experiment a "Blank" set of identical tubes should be made up using the hybridization reagents without labeled probe or target nucleic acid.

Ten microliter aliquots of each tube are pipetted into 12×75 mm polystyrene tubes; the number of such tubes is equal to the number of time points to be analyzed, plus three tubes for T0 determinations, as described above.

The three T0 replicate tubes are given 200 µl 0.4N HCl, 0.1% (v/v) $H_2O_2$, followed by 100 µl of Hydrolysis Buffer. The tubes are then read in the luminometer, using a single injection of 1N NaOH, over a period of 5 seconds. The reagent "Blank" controls, containing 10 µl of PSB alone, are prepared in a set of 3–6 tubes and treated the same way as the T0 controls.

The "Hybrid" and "Control" tubes are also given 100 µl of Hydrolysis Buffer, mixed, and placed in a circulating water bath at the desired temperature, e.g., 60° C. The timer is started.

At the desired time points, one tube from each set is given 200 µl of 0.4N HCl, 0.1% (v/v) $H_2O_2$, removed from the water bath and mixed. The tubes are allowed to sit at room temperature for at least one minute.

The chemiluminescence of the time point samples from each set of tubes is measured in a luminometer using an injection of 1N NaOH. The emitted light is measured for 5 seconds.

The data is analyzed as described above. The hybrid hydrolysis rate, expressed as the half-life (T½) in minutes, is divided by the control hydrolysis rate to obtain the differential hydrolysis (DH) ratio. These results are summarized in Table 2 below.

TABLE 2

| HYDROLYSIS CHARACTERISTICS | | | | | |
|---|---|---|---|---|---|
| | t1/2 (min) | | Rate of Hydrolysis | | |
| Compound | Temp. | pH | Hybrid | Control | Ratio |
| Std-AE | 60° C. | 7.6 | 18.1 | 0.67 | 27.0 |
| Naphthyl-AE | 60° C. | 7.6 | 5.32 | 0.52 | 10.2 |
| o-di-Br | 60° C. | 9.1 | 12.7 | 1.23 | 10.3 |
| 1-Me | 60° C. | 7.6 | 215 | 2.0 | 108 |
| 4,5-di-Me-AE | 60° C. | 9.1 | 99.7 | 0.65 | 154 |
| 2,7-di-Me-AE | 60° C. | 9.1 | 77.0 | 0.88 | 87.8 |
| o-Me-AE | 60° C. | 9.1 | 13.3 | 0.25* | 53.2 |
| | | | | 2.80* | 4.8 |
| o-MeO(cinnamyl)-AE | 60° C. | 7.6 | 63.2 | 2.1 | 30.2 |

TABLE 2-continued

HYDROLYSIS CHARACTERISTICS

| | t1/2 (min) | | Rate of Hydrolysis | | |
|---|---|---|---|---|---|
| Compound | Temp. | pH | Hybrid | Control | Ratio |
| o-MeO-AE | 60° C. | 7.6 | 27.8 | 0.92 | 30.2 |
| ortho-AE | 60° C. | 7.6 | 12.7 | 1.23 | 10.3 |
| o-F-AE | 55° C. | 7.6 | 57.7 | 0.92 | 62.4 |
| 1-Me-o-F-AE | 55° C. | 7.6 | 111 | 3.19 | 34.9 |
| 2,7-diMe-o-F-AE | 55° C. | 7.6 | 317 | 8.99 | 35.3 |
| 1-Me-m-diF-AE | 55° C. | 7.6 | 179 | 2.24 | 79.9 |

*biphasic

From the data presented in Table 1, it was found that sets of compounds could be selected, the members of which have sufficiently distinct chemiluminescent properties to be used as labeling reagents for the simultaneous detection of more than one analyte in the same tube. Surprisingly, as illustrated in Table 2, Applicants found that some of these sets also contained member compounds having similar hydrolysis characteristics; i.e., the hybridized AE label was not only preferentially protected from hydrolysis as compared to the unhybridized label but the rates of hydrolysis of the members within certain potential sets were substantially similar. FIGS. 2A and 2B show a listing of examples of sets comprising pairs of such member compounds. The examples cited therein are in no way intended to limit the present invention to these embodiments. Although these Figures illustrate the potential applicability of AE derivatives as combined pairs of labeling reagents it will be understood that sets of greater than two member compounds may be designed using the selection criteria listed in these Figures and disclosure. Moreover, the fact that certain member compounds are grouped in a set together should not in any way be taken to mean that these are the optimal or sole groupings of these particular compounds, or that other compounds would not also function as indicated. The present invention is defined solely by the claims. The acridinium ester sets listed in FIGS. 2A and 2B are candidates for use in at least one mode of the present invention.

EXAMPLE 3

Mode 1: Constant pH, Simultaneous Reaction Initiation

There are several modes in which the chemiluminescent signals of labeling reagents can be used to detect more than one nucleic acid analyte in a single sample tube according to the present invention. This and the following examples are illustrations of such modes. However, by those examples Applicants do not intend to limit the number or description of possible assay modes, or the composition or combination of labeling reagents for use in the present invention.

A first experiment tested the chemiluminescence characteristics of the AE labeling reagents coupled to single-stranded oligonucleotides in the absence of a target nucleic acid. Single-stranded oligonucleotides were designed to be complementary to RNA targets derived from *Escherichia coli* or *Chlamydia trachomatis*. The oligonucleotides were labeled as described above: the o-diBr derivative was coupled to an oligonucleotide specifically complementary to *E. coli* target RNA, while a mixture of the 1- and 3-Me derivatives were used to label an oligonucleotide specifically complementary to *C. trachomatis* target RNA. The labeled oligonucleotides were diluted into 10 mM lithium succinate (pH 5.0) and 0.1% (w/v) lithium lauryl sulfate such that 10 µl of the resulting solution contained about 200,000 RLU (approximately 0.002 pmoles) of each oligonucleotide. Ten microliters of each oligonucleotide were combined with 10 µl of the same dilution buffer in separate tubes; additionally, 10 µl of each labeled oligonucleotide were combined in a single tube. Two hundred microliters of a solution containing 0.1N HCl, 0.1% $H_2O_2$ were given to the tube, followed by 100 µl of a solution containing 0.19M $Na_2B_4O_7$ (pH 7.6) and 5% (v/v) TRITON® X-100 detergent (polyoxyethylene ether. The resulting solution was placed into a LEADER® 50 luminometer, and chemiluminescence was measured at various intervals following injection of 200 µl of 1N NaOH into the sample solution. The luminometer was placed in "kinetic analysis" mode during the experiment; this allowed the collection of RLU data points at predetermined time intervals after initiation of the chemiluminescence reaction.

In another experiment, the same labeled oligonucleotides were each hybridized with an excess of their respective target RNA as described in Nelson et al., supra, previously incorporated by reference herein. The hybridization was performed in a 50 µl reaction volume and incubated at 55° C. for 60 minutes. The final solution for hybridization contained 100 mM lithium succinate (pH 5.2), 8.5% (w/v) lithium lauryl sulfate, 1.5 mM EDTA and 1.5 mM EGTA. Tubes containing 50 µl of each individual probe:target hybridization mixture alone, or a combination of both hybridization mixtures, were given 150 µl of 0.19M sodium tetraborate (pH 7.6) in 5.0% (v/v) TRITON® X-100 detergent. The final amount of each labeled oligonucleotide was about 0.002 pmoles for each experimental tube. The samples were placed into a LEADER® 50 luminometer, and chemiluminescence was initiated with the addition of 200 µl of 0.1% (v/v) $H_2O_2$ in 1 mM $HNO_3$ and, after a 0.1 to 2 second delay, an automatic injection of 200 µl of 1N NaOH. Chemiluminescence was measured for various times. Again, the luminometer was placed in "kinetic analysis" mode during the experiment; this allowed the collection of RLU data points at predetermined time intervals after initiation of the chemiluminescence reaction.

The data gathered for the unhybridized labeled oligonucleotides is shown in Table 3 below.

TABLE 3

| Interval Number | o-diBr-AE | 1 or 3-Me-AE | o-diBr-AE + 1 or 3-Me-AE |
|---|---|---|---|
| 1 | 244 | 35 | 704 |
| 2 | 19152 | 293 | 21995 |
| 3 | 41101 | 1882 | 40563 |
| 4 | 44573 | 4056 | 45306 |
| 5 | 33485 | 6496 | 34719 |
| 6 | 17325 | 8004 | 23182 |
| 7 | 12622 | 8648 | 20631 |
| 8 | 6118 | 9346 | 16696 |
| 9 | 2345 | 9300 | 12626 |
| 10 | 956 | 8769 | 10243 |
| 11 | 521 | 8376 | 9392 |
| 12 | 360 | 7727 | 8498 |
| 13 | 262 | 7314 | 7860 |
| 14 | 225 | 6822 | 7334 |
| 15 | 187 | 6358 | 6858 |
| 16 | 161 | 5950 | 6463 |
| 17 | 142 | 5457 | 5935 |
| 18 | 133 | 5149 | 5489 |
| 19 | 116 | 4776 | 5071 |
| 20 | 106 | 4454 | 4840 |
| 21 | 93 | 4111 | 4448 |
| 22 | 86 | 3840 | 4155 |
| 23 | 83 | 3575 | 3915 |

TABLE 3-continued

| Interval Number | o-diBr-AE | 1 or 3-Me-AE | o-diBr-AE + 1 or 3-Me-AE |
|---|---|---|---|
| 24 | 73 | 3320 | 3615 |
| 25 | 62 | 3089 | 3370 |
| 26 | 58 | 2852 | 3157 |
| 27 | 57 | 2675 | 2927 |
| 28 | 51 | 2477 | 2781 |
| 29 | 52 | 2296 | 2533 |
| 30 | 53 | 2139 | 2410 |
| 31 | 46 | 1996 | 2230 |
| 32 | 43 | 1855 | 2063 |
| 33 | 39 | 1702 | 1921 |
| 34 | 37 | 1592 | 1790 |
| 35 | 33 | 1468 | 1669 |
| 36 | 37 | 1381 | 1563 |
| 37 | 35 | 1289 | 1456 |
| 38 | 33 | 1189 | 1358 |
| 39 | 29 | 1101 | 1278 |
| 40 | 30 | 1035 | 1191 |
| 41 | 26 | 962 | 1119 |
| 42 | 26 | 891 | 1031 |
| 43 | 26 | 846 | 974 |
| 44 | 25 | 765 | 905 |
| 45 | 25 | 730 | 841 |
| 46 | 20 | 689 | 797 |
| 47 | 21 | 638 | 742 |
| 48 | 18 | 581 | 700 |
| 49 | 19 | 539 | 655 |
| 50 | 20 | 503 | 597 |

In this experiment the chemiluminescence was measured for a total of 2 seconds with readings at intervals of 0.04 seconds. The results show that the o-diBr-AE label has a sharp peak of light emission which occurs very quickly after the initiation of the chemiluminescence reaction. The peak of light emission under these conditions is at interval 4; about 0.16 seconds after initiation, and then the signal decays rapidly. By contrast, the light emitted by the mixture of 1- and 3-Me-AE derivative peaks at about interval 8 (0.32 seconds after initiation) and decays slowly thereafter. Moreover, in the later intervals (intervals 14–50, and particularly intervals 41–50) the signal from the o-diBr-AE derivative is almost zero while the signal from the 1- and 3-Me mixture is still significantly greater than background. The data from the sample containing both labels approximates the sum of the two individual data sets at each point.

The data obtained from the experiments involving the hybridized samples of the two labeled oligonucleotides is shown in Table 4 below.

TABLE 4

| Interval Number | o-diBr—AE | 1 or 3-Me—AE | o-diBr—AE + 1 or 3-Me—AE |
|---|---|---|---|
| 1 | 1082 | 0 | 464 |
| 2 | 21715 | 208 | 19608 |
| 3 | 46504 | 1242 | 49854 |
| 4 | 53824 | 3104 | 55250 |
| 5 | 49288 | 5474 | 50275 |
| 6 | 35382 | 7902 | 39082 |
| 7 | 28444 | 10110 | 36476 |
| 8 | 26001 | 12063 | 35488 |
| 9 | 20463 | 13638 | 30522 |
| 10 | 13750 | 14681 | 24878 |
| 11 | 8712 | 15476 | 21894 |
| 12 | 5460 | 15892 | 20156 |
| 13 | 3566 | 16138 | 19170 |
| 14 | 2438 | 16180 | 18450 |
| 15 | 1802 | 16048 | 17786 |
| 16 | 1402 | 15756 | 17146 |

TABLE 4-continued

| Interval Number | o-diBr—AE | 1 or 3-Me—AE | o-diBr—AE + 1 or 3-Me—AE |
|---|---|---|---|
| 17 | 1106 | 15416 | 16362 |
| 18 | 899 | 15044 | 15840 |
| 19 | 765 | 14470 | 15062 |
| 20 | 648 | 14001 | 14426 |
| 21 | 560 | 13444 | 13754 |
| 22 | 484 | 12986 | 12128 |
| 23 | 430 | 12438 | 12516 |
| 24 | 380 | 11923 | 11950 |
| 25 | 334 | 11444 | 11337 |
| 26 | 308 | 10931 | 10856 |
| 27 | 274 | 10382 | 10311 |
| 28 | 250 | 9926 | 9816 |
| 29 | 230 | 9598 | 9346 |
| 30 | 200 | 9093 | 8838 |
| 31 | 185 | 8692 | 8480 |
| 32 | 172 | 8306 | 8040 |
| 33 | 154 | 7916 | 7680 |
| 34 | 141 | 7587 | 7291 |
| 35 | 144 | 7232 | 6896 |
| 36 | 128 | 6912 | 6614 |
| 37 | 128 | 6567 | 6295 |
| 38 | 114 | 6238 | 5960 |
| 39 | 103 | 5980 | 5658 |
| 40 | 100 | 5695 | 5450 |
| 41 | 96 | 5384 | 5165 |
| 42 | 96 | 5136 | 4900 |
| 43 | 88 | 4932 | 4688 |
| 44 | 79 | 4697 | 4430 |
| 45 | 81 | 4522 | 4230 |
| 46 | 75 | 4280 | 4037 |
| 47 | 75 | 4043 | 3850 |
| 48 | 71 | 3901 | 3683 |
| 49 | 65 | 3680 | 3486 |
| 50 | 66 | 3532 | 3318 |

The time intervals were the same as in Table 3. In this case, the difference between the emission characteristics of the two labels was even more clearly distinguishable than in the previous experiment: the peak of E. coli-hybridized o-diBr-AE occurs again in about interval 4; however, the peak for C. trachomatis-hybridized 1-Me-AE is at approximately interval 14. Again, during the later intervals (particularly intervals 41–50) the signal obtained from the o-diBr-AE derivative is almost gone, while the signal from the 1-Me-AE derivative is still significant. And again the profile of the sample containing a mixture of the 2 hybridized labeled oligonucleotides approximates the sum of the two individual sample profiles at each point.

These data demonstrate the applicability and utility of one mode of the method and compositions of the present invention. The signal obtained in a single test tube containing two different oligonucleotides labeled with specific AE derivatives as set forth in the present example is clearly made up of two components, one contributed by a quickly reacting, quickly decaying species (for example, the o-diBr-AE), and the other contributed by a species which is slower to react and decay (for example, the 1- and 3-Me-AE mixture). By designing two detection time periods for analysis, an early one (for example intervals 1–6; 0.04–0.24 seconds) for the detection of analyte associated with the quickly-reacting species and a late one (for example, intervals 41–50; 1.64–2.0 seconds) for the detection of analyte associated with the slowly-reacting species, the method and reagents of the present invention permit virtually simultaneous detection of different nucleic acid sequences in a single sample.

The raw data obtained from this experiment was treated further using a reiterative data analysis method as follows. Samples containing only one labeled probe were used as standards for data analysis. For each standard the ratio between the sum of the RLU values obtained in intervals 1–10 and the sum of the RLU values obtained in intervals 41–50 was determined (Σ RLU 41–50/Σ RLU 1–10); for o-diBr-AE this ratio was 0.00267 and for 1-Me-AE the ratio was 0.645. The chemiluminescent signals measured in intervals 41–50 (in RLU) were added together and then divided by 0.645, the ratio obtained for the 1- and 3-Me standard. The resulting figure is the amount of RLU contributed in intervals 1–10 by 1- and 3-Me-AE-labeled probe. This amount, subtracted from the total RLU in intervals 1–10, gives the amount of RLU contributed in these intervals by o-diBr-AE. The latter number, when multiplied by 0.00267 (the ratio for o-diBr-AE), yields the RLU within the intervals 41–50 which were contributed by o-diBr-AE-labeled probe. When this figure is subtracted from the total RLU in intervals 41–50, a corrected value for the RLU contributed by 1-Me-AE in this interval is yielded. This number was used to repeat the calculation described above until the RLU contribution by o-diBr-AE in intervals 41–50 did not change within the chosen number of significant figures. An illustration of the method, as applied to the raw data of Table 5, is indicated below.

TABLE 5

| Observed RLU | | Initial Calculation | | First Correction | | Second Correction | |
|---|---|---|---|---|---|---|---|
| Intervals | Sum. | 1-Me | diBr | 1-Me | diBr | 1-Me | diBr |
| 1–10 | 341,896 | 64,788 | 277,108 | 63,639 | 278,257 | 63,631 | 278,265 |
| 41–50 | 41,788 | 41,788 | 741 | 41,047 | 746 | 41,042 | 746 |

A personal computer was programmed to perform these calculations. The raw data was fed directly from the luminometer into the computer using the machine's RS-232 port, and the data processed as described above. The intervals used in the above analysis may differ depending on the labeling reagent chosen and it is not mandatory that the specific intervals illustrated above or in the following examples be used. Moreover, while the data analysis method disclosed in this example was performed on data obtained in experiments using two chemiluminescent compounds, it will be clear to one of skill in the art that these same methods can be used to process data obtained from more than two such compounds provided that the reaction characteristics of each compound are sufficiently different from the others.

EXAMPLE 4

Mode 2: Sequential Reaction at Different pH Values

In another mode the reagents and method of the present invention may be used to detect and measure more than one analyte in a sample by initiating the chemiluminescence reaction at different pH values. At the first pH, chemiluminescent reactions may be initiated, for example by the addition of sodium peroxide and base in an appropriate buffer, causing one or more of the labeling reagents to emit measurable light while one or more additional labeling reagents will not react to an appreciable extent at that pH. The amount of light emitted at the first pH may be measured in a luminometer. Additionally, the emitted light may be measured over a period of time, and the time period may be divided into intervals as detailed above for a kinetic analysis of the reaction. After measurement at a given pH, the pH of the test solution may be adjusted to a value at which one or more other chemiluminescent labeling reagents may react.

While the data presented herein illustrates this mode of the invention using two AE derivatives, it will be clear to one skilled in the art in light of this disclosure that more than two pH values may be used in the method of this invention. Moreover, in light of this disclosure it will also be clear to one skilled in the art that aspects of the various modes described herein may be combined in a single assay system. For example, at each pH value of the "multiple pH" mode described in this example, a set of kinetically distinct labels may be detected in a manner according to the previous example. Such a system would thus allow for the detection of three or more analytes in the same sample tube. Other combinations, not expressly mentioned, will also be clear to one of ordinary skill in the art. All such combinations, whether expressly mentioned herein or not, are intended to fall within the scope of the present invention.

Two oligonucleotides, each labeled with an AE derivative having a different optimum pH for the chemiluminescent reaction, were singly diluted into a solution containing 10 mM lithium succinate (pH 5.0) and 0.1% (w/v) lithium lauryl sulfate. The first oligonucleotide, specific to *Chlamydia trachomatis* 16S rRNA, was coupled via a linker arm to standard AE. The second oligonucleotide, specific to *Chlamydia trachomatis* 23S rRNA, was coupled via a linker arm to o-F-AE. Ten microliters (about 0.002 pmoles) of each oligonucleotide was combined with 10 $\mu$l of the same dilution buffer in separate tubes; additionally, 10 $\mu$l of each labeled oligonucleotide were combined in a single tube. Each tube was given 40 $\mu$l of 0.4N HCl, 60 $\mu$l water and 200 $\mu$l of a solution containing 1 mM $HNO_3$ and 0.1% $H_2O_2$. The tubes were placed into a LEADER® 50 luminometer (Gen-Probe Incorporated, San Diego, Calif.), and chemiluminescence was measured with the automatic injection of 200 $\mu$l of 0.24M boric acid (adjusted to pH 12.9 with NaOH). The approximate pH of the solution at this point was 12.1. The chemiluminescence was measured for 8 seconds followed by another automatic injection of 200 $\mu$l of 0.75N NaOH to an approximate final pH of 13.0. The resulting chemiluminescence was measured for 10 seconds. During the measurement of chemiluminescence data was collected in 0.1 second intervals and immediately downloaded into a IBM-compatible PC computer. The data was then plotted as RLU versus time (interval number).

Figure 3A:
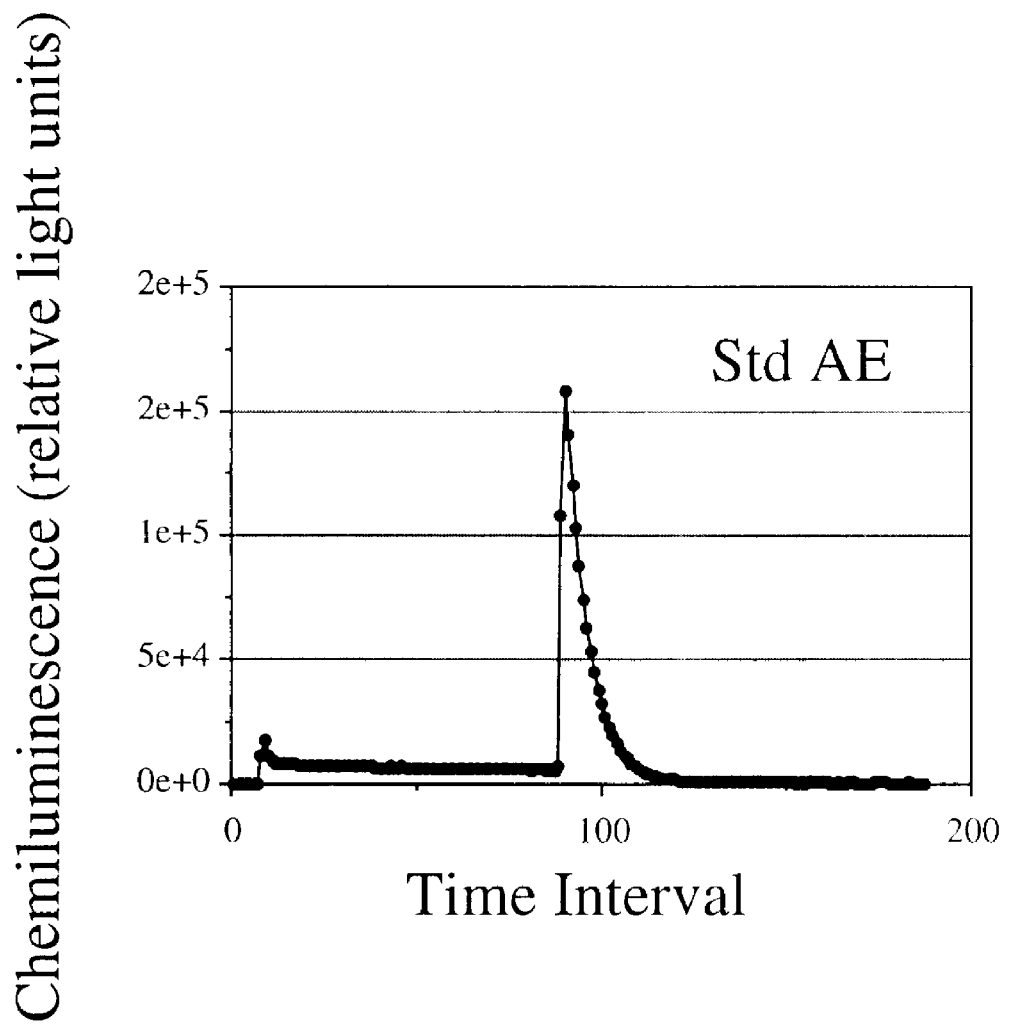
FIGS. 3A, 3B through 3C are a graphically representation of an example using two labeling reagents in a multiple pH mode of the present invention. In each of FIGS. 3A–C a triggering reagent was added to the solution at about interval 5, and the reaction mixtures were shifted from approximately pH 12.1 to approximately pH 13.0 at about time interval 90, shown as the X-axis of the graph.
Figure 3B:
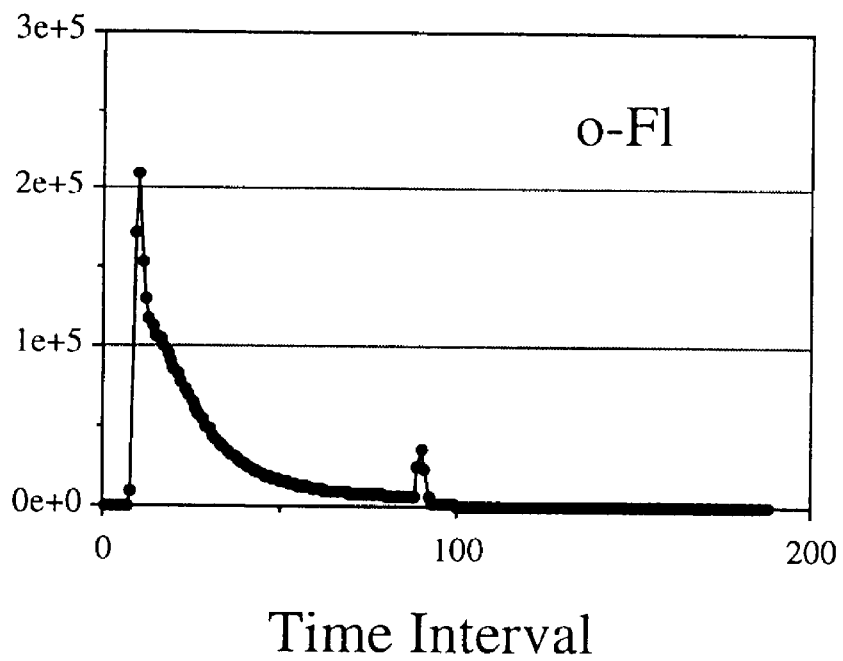
Figure 3C:
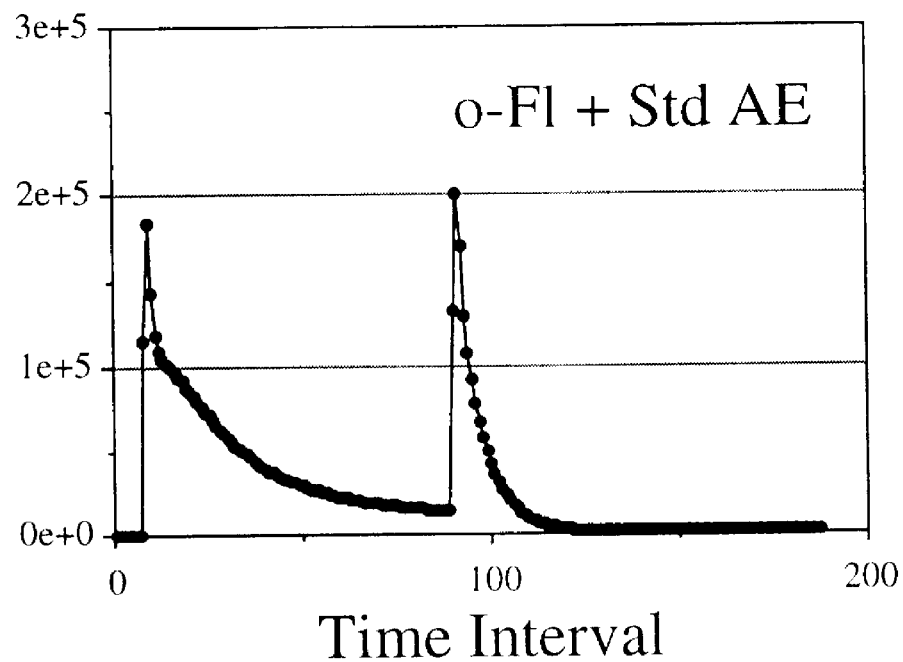

The results are shown in FIGS. 3A, 3B and 3C. These data show that more than one chemiluminescent labeling reagent coupled to an oligonucleotide can be detected as a member of a set of such labeling reagents chosen on the basis of their optimal pH for reaction.

EXAMPLE 5

Simultaneous Detection of *Chlamydia trachomatis* and *Neisseria gonorrhoeae* Nucleic Acids in a Homogeneous Assay Format The method and compositions of the present invention were used to simultaneously detect the presence of nucleic acids derived from *Chlamydia trachomatis* (Ctr) and *Neisseria gonorrhoeae* (Ngo) in a single test sample spiked with known amounts of the target nucleic acids. In this example the formation, selection, and detection of labeled analyte/probe conjugates was carried out solely in the liquid phase.

For convenience's sake, the Ctr and Ngo-specific probes were those used in Gen-Probe's commercially available PACE® 2 assay (Gen-Probe Incorporated, San Diego, Calif.). In the commercially available assay the Ctr and Ngo probes are each labeled with standard AE (see FIG. 1) and assayed separately. By contrast, in the example described herein the commercially available Ctr probes were replaced with the identical probes labeled with 1- and 3-Me-AE, and the standard Ngo probes were replaced with the identical probes labeled with a mixture of 1- and 3-Me-m-diF-AE. Moreover, as in the commercially available PACE® 2 assay, the labeled probes were used together in a "probe mix" with other non-labeled helper probes designed to accelerate the rate of hybridization and the stability of the formed hybrid nucleic acid. The use of helper probes is described above and in U.S. Pat. No. 5,030,557. As stated above, helper probes are not necessary for the practice of the present invention although helper probes may be necessary in conjunction with the use of particular labeled hybridization probes. Also, as mentioned above, the present invention does not depend on the particular nucleotide sequences of the nucleic acid analyte or the hybridization assay probe; thus the specific oligonucleotide probes used in these examples are not an essential feature of the present invention. The present methods and compositions can be used with any set of two or more nucleic acid analyte/hybridization probe pairs which form mutually exclusive stable double-stranded hybrids.

Samples were prepared for the assay by adding different amounts of Ctr and Ngo ribosomal RNA targets to a solution containing 3% (w/v) lithium lauryl sulfate, 30 mM sodium phosphate buffer (pH 6.8), 1 mM EDTA, 1 mM EGTA to a final volume of 50 μl. The probe reagent was prepared by combining the 1-Me-AE-labeled Ctr probe with 1-Me-m-diF-AE-labeled Ngo probe in a solution containing 200 mM lithium succinate (pH 5.1), 17% (w/v) lithium lauryl sulfate, 3 mM EDTA, 3 mM EGTA. The total amount of the probes labeled with each of the AE derivatives was about 0.2 pmoles.

Each hybridization reaction mixture contained 50 μl of the target nucleic acids (or in control experiments, no target) and 50 μl of the probe reagent. Each reaction mixture was incubated at 55° C. for one hour. Three hundred microliters of 0.15M sodium tetraborate (pH 8.5), 2% (v/v) TRITON® X-100 detergent were added to each sample, and the samples incubated at 55° C. for 20 minutes. Chemiluminescence of each sample was measured in a LEADER® 50 luminometer with the automatic injection of 200 μl of a solution containing 0.1% $H_2O_2$, 1 mM $HNO_3$, followed after a 2 second delay by another injection of 1N NaOH, 2% (w/v) Zwittergent® $^3$-14 (N-tetradecyl-N,N-dimethyl-3-ammonio-1-propane-sulfonate; ZWITTERGENT® 3–4 detergent is a registered trademark of CalBiochem, La Jolla, Calif.). The chemiluminescence of each sample was monitored for 2 seconds using the luminometer's kinetic mode and intervals of 0.04 seconds. The data were transferred directly from the luminometer into a personal computer and analyzed using calculation methods similar to those described in Example 3 above. The time intervals used for these calculations were intervals 1–6 and 41–50. Two standards for each different label were averaged, as were two blank samples, which contained no probe or target nucleic acids. The RLU value obtained in each time interval for the averaged blank standards was subtracted from the RLU values for the corresponding interval for all other samples prior to calculation. Each sample was run in duplicate; values shown are the average of the duplicate reaction mixtures. The results are shown in Table 6 below.

TABLE 6

| [Ngo] (fmol) | [Ctr] (fmol) | Total measured RLU | Calculated Values | |
|---|---|---|---|---|
| | | | 1-Me-m-diF—AE—[Ngo] | 1-Me—AE—[Ctr] |
| 10 | 0 | 102330 | 102857 | 243 |
| 2.5 | 0 | 28872 | 27769 | 948 |
| 0.5 | 0 | 7624 | 5533 | 2078 |
| 0 | 3.0 | 103193 | 0 | 110774 |
| 0 | 0.75 | 29865 | 640 | 30419 |
| 0 | 0.15 | 7446 | 266 | 7510 |
| 10 | 3.0 | 202729 | 98729 | 116462 |
| 10 | 0.75 | 124013 | 89825 | 36738 |
| 10 | 0.15 | 102883 | 102238 | 4411 |
| 2.5 | 3.0 | 134348 | 28441 | 115172 |
| 2.5 | 0.75 | 56553 | 23564 | 37321 |
| 2.5 | 0.15 | 35038 | 27282 | 8531 |
| 0.5 | 3.0 | 109582 | 2317 | 118248 |
| 0.5 | 0.75 | 33385 | 4223 | 33129 |
| 0.5 | 0.15 | 12490 | 5959 | 7449 |
| 0 | 0 | 2089 | 355 | 1811 |

These data indicate that at least two analytes (Ctr and Ngo ribosomal RNA in this example) can be identified, either alone or in a sample together, using the multiple analyte method and reagents of the present invention.

EXAMPLE 6

Simultaneous Detection of *Chlamydia trachomatis* and *Neisseria gonorrhoeae* Nucleic Acids in a Mixed Homogeneous/Heterogeneous Assay Format The method of the present invention was again used to simultaneously detect the presence of Ctr and Ngo in a "pure system" (i.e., no clinical specimen present); this time in a mixed homogeneous/heterogeneous assay system. The assay used for this example was the PACE® 2 format (commercially available from Gen-Probe Incorporated, San Diego, Calif.), modified as described herein. The probes used in this assay were identical to those used in Example 5 and were used in a probe mix with helper probes.

For the assay, different amounts of either Ngo or Ctr ribosomal RNA, or both, were combined in each tube; the amounts of target varied between 0 and 12.5 fmoles. Final volume of each target nucleic acid dilution was 100 μl; the difference in volume was made up with a solution of 30 mM sodium phosphate (pH 6.8), 3% (w/v) lithium lauryl sulfate, 1 mM EDTA, 1 mM EGTA. The probe reagent was prepared by mixing the 1-Me-AE probe mix and the 1-Me-m-diF-AE probe mix in equal volumes; as in the previous experiment, the probe reagents also contained helper probes. The probe mix contained 190 mM lithium succinate (pH 5.1), 17% (w/v) lithium lauryl sulfate, 3 mM EDTA, 3 mM EGTA and the probes; one hundred microliters of this was added to the target nucleic acid dilutions to yield a final volume of 200 μl. The tubes were shaken to mix and incubated at 60° C. for 90 minutes. The tubes were removed from the water bath and given 1 ml of a solution of 190 mM sodium tetraborate (pH 7.6), 6.89% (w/v) TRITON® X-102 (polyoxyethylene ether) and 0.01% (w/v) gelatin containing 50 μl of a 1.25% (w/v) suspension of Biomag® 4100 magnetic particles (PerSeptive Biosystems, Cambridge, Mass.) in 0.02% (w/v) sodium azide and 1 mM EDTA. The tubes were incubated further at 60° C. for 10 minutes then removed from the water bath, and the rack was immediately placed on a magnetic separation base and allowed to stand at room temperature for 5 minutes, then the unbound probe was separated from the magnetic bead-bound hybridized probe by decanting the solution. See, Arnold, et al., European Publication No. EPO 281390, which enjoys common ownership with the present invention and which is hereby incorporated by reference herein. The beads and adsorbed hybridized probe were washed once in a solution of 20 mM sodium tetraborate (pH 10.4), 0.1% (w/v)-ZWITTERGENT® 3–14 detergent, then resuspended in 300 μl of 5% (v/v) TRITON® X-100 detergent.

Each sample was then loaded into a LEADER® 50 luminometer. The chemiluminescent reaction was initiated with the automatic injection of 200 μl of a solution containing 0.1% (v/v) $H_2O_2$, 1 mM $HNO_3$, followed after a 2 second delay by another injection of 200 μl of a solution containing 0.7N NaOH, and 0.5% (v/v) ZWITTERGENT® 3–14 detergent. The chemiluminescence of each sample was monitored for 2 seconds using the luminometer's kinetic mode and intervals of 0.04 seconds. The data were transferred directly from the luminometer into a personal computer and analyzed using calculation methods similar to those described in Example 3 above. The time windows used for these calculations were from intervals 1–7 and 34–50. Two standards for each different label were averaged (using 5 fmoles ribosomal RNA for the Ngo control and 1.5 fmoles ribosomal RNA for the Ctr control), as were two blank samples, which contained no probe or target nucleic acids. The RLU value obtained for the averaged blank standards in each time interval was subtracted from the RLU values for all other samples for the corresponding interval prior to calculation. Each sample was run in duplicate; values shown are the average of the duplicate reaction mixtures. The results are shown in Table 7 below.

TABLE 7

| [Ngo] (fmol) | [Ctr] (fmol) | Total RLU | Calculated Values | |
|---|---|---|---|---|
| | | | 1-Me-m-diF-AE-[Ngo] | 1-Me-AE-[Ctr] |
| 12.5 | 0 | 254925 | 257767 | 175 |
| 1.25 | 0 | 36362 | 38501 | 101 |
| 0.125 | 0 | 4197 | 4055 | 95 |
| 0 | 3.5 | 272939 | 0 | 291493 |
| 0 | 0.35 | 32857 | 67 | 32608 |
| 0 | 0.035 | 3785 | 0 | 4424 |
| 12.5 | 0.35 | 288682 | 248593 | 32160 |
| 12.5 | 0.035 | 256085 | 242548 | 3663 |
| 1.25 | 3.5 | 307178 | 31796 | 286008 |
| 1.25 | 0.35 | 66359 | 34839 | 32301 |
| 1.25 | 0.035 | 38674 | 36768 | 3273 |
| 0.125 | 3.5 | 288682 | 4785 | 287861 |
| 0.125 | 0.35 | 36157 | 3522 | 33555 |
| 0.125 | 0.035 | 7601 | 3906 | 3605 |
| 0 | 0 | 317 | 0 | 92 |

These data demonstrate that by using the compositions and methods of the present invention more than one analyte (Ctr and Ngo ribosomal RNA in this case) can be clearly identified alone or combined in the same sample tube. Moreover, when the probes containing the labeling reagents of the present invention are combined in the same sample tube, the same sample volume is sufficient for the nearly simultaneous identification of more than one analyte using the present invention. This permits saving any remaining sample for other purposes (such as other assays) thereby increasing the number of assays that can be done using samples of a given volume. Additionally, the data listed above show that an assay conducted in accordance with this embodiment of the present invention has high sensitivity, with a sensitivity limit in this experiment of at least 0.125 fmole for Ngo and 0.035 fmole for Ctr. By presenting the data in this Example Applicant does not intend to imply, however, that this is the lower limit of sensitivity obtainable under any set of experimental conditions.

EXAMPLE 7

Simultaneous Detection of *Chlamydia trachomatis* and *Neisseria gonorrhoeae* ribosomal RNA in a Clinical Specimen The method and reagents of the present invention were used to simultaneously detect the presence of Ctr and Ngo ribosomal RNA in a clinical specimen. The assay format was the same as used in Example 6 with the following differences.

Each sample was prepared by adding the desired amount of ribosomal RNA to 100 μl of a pool of endocervical swab clinical specimens; each swab had been originally suspended in a volume of 1 ml of Gen-Probe PACE® 2 transport medium (obtainable as a component of the STD Transport Kit from Gen-Probe Incorporated, San Diego, Calif.). These specimens had previously tested negative for Ctr and Ngo. Had the original clinical samples contained Ctr or Ngo cells, these cells would have been lysed and their nucleic acids (including ribosomal RNA) released into solution by the action of components of the transport medium.

Hybridization was conducted as in Example 5, but was lengthened to 2.5 hours. Following hybridization, chemiluminescence was measured as described in Example 6, except for the following changes. A solution of 0.5N NaOH and 0.5% Zwittergent® was substituted for 0.7N NaOH and 0.5% ZWITTERGENT® 3–14 detergent; the Ngo and Ctr ribosomal RNA standards were 1.25 fmoles and 0.35 fmoles, respectively; and the intervals chosen for the time windows were intervals 1–5 and 41–50. Assay results are shown in Table 8 below.

TABLE 8

| [Ngo] (fmol) | [Ctr] (fmol) | Total RLU | Calculated Values | |
|---|---|---|---|---|
| | | | 1-Me-m-diF-AE-[Ngo] | 1-Me-AE-[Ctr] |
| 5 | 0 | 87204 | 79613 | 186 |
| 0.5 | 0 | 9909 | 7825 | 62 |
| 0.05 | 0 | 1403 | 1019 | 62 |
| 0 | 5 | 179368 | 2 | 180452 |
| 0 | 0.5 | 20892 | 12 | 20222 |
| 0 | 0.05 | 2285 | 2 | 1985 |
| 5 | 5 | 258886 | 69936 | 174931 |
| 5 | 0.5 | 92174 | 57232 | 20408 |
| 5 | 0.05 | 81031 | 70362 | 2109 |
| 0.5 | 5 | 189936 | 9776 | 188578 |
| 0.5 | 0.5 | 26500 | 6887 | 17865 |
| 0.5 | 0.05 | 10625 | 6887 | 1736 |
| 0.05 | 0.5 | 19758 | 590 | 18609 |
| 0.05 | 0.05 | 3208 | 939 | 1985 |
| 0 | 0 | 366 | 23 | 93 |

These data demonstrate that the ability of the method and reagents of the present invention to permit the detection and quantification of more than one analyte in a single sample is not defeated by substances present in a pool of clinical samples.

EXAMPLE 8

Detection of the gag and pol Regions of HIV DNA

The method of the present invention was used to simultaneously detect the gag and pol regions of the human immunodeficiency virus (HIV) genome. An advantage of the multiple analyte detection feature of the present invention for the identification of HIV is that detection of the presence of the second region (either gag or pol) of the HIV genome can be used to confirm the presence of the virus in a diagnostic assay by virtue of the reduced likelihood of two simultaneous false positive assay indications in the same assay. Moreover, the detection of more than one distinct nucleotide sequence of the same nucleic acid analyte can help to ensure detection of a virus or cell in cases where one target nucleotide sequence has varied or mutated.

In the present example, a region of the HIV genome containing both the gag and pol regions was first amplified as described below. The gag and pol nucleotide sequence regions were then simultaneously detected using the method and reagents of the present invention in a hybridization protection assay (HPA) format.

Probes complementary to the gag and pol regions of the HIV-1 genome were synthesized. The gag-specific probe (SEQ ID NO: 11) was labeled with a mixture of 1- and 3-Me-AE and the pol-specific probe (SEQ ID NO: 5) was labeled with o-diBr-AE, also as described above, using a non-nucleotide linker arm incorporated as part of the oligonucleotide during synthesis to join the label to the probe. A cloned HIV-1 DNA fragment containing both target sequence regions was amplified in a 100 µl volume as described in Kacian, et al., PCT Publication No. WO 91/01384 which enjoys common ownership with the present application, and which is incorporated by reference herein. Amplification primers used to amplify the pol region had nucleotide sequences SEQ ID NOs: 1 through 4. Probes and primers which are used to amplify the gag region have nucleotide sequences SEQ ID NOs: 5 through 10.

Following amplification of the HIV-1 DNA, the probes were hybridized to the gag and pol target nucleic acid regions by adding 100 µl of a solution containing 5.5 fmol of the 1-Me-AE labeled gag probe and 16 fmol of the o-diBr-AE labeled pol probe in 0.2M lithium succinate (pH 5.0), 17% (w/v) lithium lauryl sulfate, 3 mM EDTA and 3 mM EGTA to the amplification reaction mixture. An unlabeled helper oligonucleotide of SEQ ID NO: 6 was also used to assist in the amplification of the pol target region. The reaction mixture was then incubated for 30 minutes at 60° C. Hydrolysis of the acridinium derivatives on the unhybridized probe was accomplished by adding 300 µl of a solution of 0.13M Na$_2$B$_4$O$_7$ (pH 9.3), 2% (v/v) TRITON® X-100 detergent, and 13 mM iodoacetic acid and incubating the mixture for 20 minutes at 60° C. At this pH iodoacetic acid is added to the reaction mixute to prevent formation of acridinium ester adducts which are unreactive in the chemiluminescent assay.

Chemiluminescence was measured in a LEADER® 50 luminometer. Each sample was placed in the luminometer, and the chemiluminescent reaction initiated by the automatic injection of 200 µl of 0.1% (v/v) H$_2$O$_2$ in 1 mM HNO$_3$, followed by a 2 second delay and automatic injection of 1.5N NaOH. Chemiluminescence was measured for 2 seconds using the luminometer's kinetic mode and intervals of 0.04 seconds. The data was collected using a personal computer, and the raw data was analyzed using the calculation methods described in Example 3. The time windows used for the calculations corresponded to intervals 1–10 and 41–50. In this case, 2 standards for each label were used (these consisted of purified nucleic acids containing the nucleotide sequence of each target; either gag alone or pol alone) as well as 2 negative controls which were treated the same as the other samples but contained no target nucleic acids or probe. Data obtained from duplicate standard samples were averaged, and all samples were corrected for background as described above. The results are shown in Table 9 below. In this experiment, a negative assay result yields an RLU value of less than 10,000. In all experiments using gag and pol target nucleic acid sequences (except the controls mentioned above), the gag and pol targets are contained once in each target nucleic acid molecule.

TABLE 9

| Input Template Nucleic Acid Sequence (before amplification) (Average # Copies) | Total Observed RLU | Calculated Values (RLU) | |
|---|---|---|---|
| | | pol | gag |
| 20 | 424149 | 163116 | 275832 |
| 20 | 474982 | 181555 | 288683 |
| 20 | 502688 | 175009 | 326109 |
| 20 | 487885 | 167060 | 343985 |
| 5 | 168892 | 72321 | 78129 |
| 5 | 275045 | 84425 | 116487 |
| 5 | 262052 | 102490 | 137456 |
| 5 | 290219 | 121739 | 140858 |
| 2.5 | 181562 | 31211 | 121724 |
| 2.5 | 221174 | 53702 | 146548 |
| 2.5 | 242543 | 115704 | 116987 |
| 2.5 | 12327 | 4205 | 8943 |
| 1.25 | 214078 | 86608 | 117385 |
| 1.25 | 7036 | 4738 | 1637 |
| 1.25 | 403548 | 112971 | 277915 |
| 1.25 | 3246 | 2265 | 497 |
| 0 | 4035 | 3019 | 508 |
| 0 | 4119 | 2634 | 2255 |
| 0 | 4396 | 3079 | 730 |
| 0 | 4340 | 2954 | 1542 |

The data show that the method of the present invention can simultaneously detect the presence of nucleic acids having sequences corresponding to the gag and pol regions of HIV-1. The listed number of copies of template nucleic acids is an average number; clearly, the number of input copies of template is an integer and not a fraction. Indeed, the data indicate that some samples contain no copies of the template, as can be seen from RLU values below 10,000 that occur in both the reaction sets corresponding to 2.5 and 1.25 copies of template. The sensitivity of this assay, which combines nucleic acid amplification with the compositions and methods of the present invention, is approximately 1 to 2 copies of each target nucleic acid sequence.

EXAMPLE 9

Detection of gag and pol Regions of HIV DNA in a Sample Containing a Clinical Specimen.

The method of the present invention was used to simultaneously detect both the gag and pol regions of the Human Immunodeficiency Virus (HIV) in a human blood lysate. Whole blood which had been previously determined to be negative for HIV was lysed, and the white blood cells were collected, washed, and lysed as described in Ryder, PCT Publication No. WO 93/25710 which enjoys common ownership with the present application, and which is incorporated by reference herein. Fifty microliters of the leukocyte lysate was used for each experimental tube. A plasmid DNA containing the gag and pol regions of HIV (see Example 8 above) was added to the lysate, and the added nucleic acid was amplified, hybridized, and subjected to differential hydrolysis as described in Example 8. Results are shown in Table 10 below.

TABLE 10

| Input Template Nucleic Acid Sequence (before amplification) (Average # Copies) | Total Observed RLU | Calculated Values (RLU) | |
|---|---|---|---|
| | | pol | gag |
| 5 | 549945 | 264861 | 199071 |
| 5 | 545940 | 271571 | 210287 |
| 2.5 | 503159 | 261827 | 185001 |
| 2.5 | 513946 | 243812 | 195769 |
| 2.5 | 523733 | 278479 | 184205 |
| 2.5 | 490689 | 265543 | 166766 |
| 2.5 | 518724 | 255322 | 199760 |
| 2.5 | 518377 | 259885 | 192783 |
| 0 | 8946 | 6296 | 4018 |
| 0 | 9113 | 5642 | 4161 |

These data indicate that the gag and pol targets can be detected simultaneously when the target nucleic acid is amplified in the presence of a cell lysate from blood mononuclear cells. In such a detection system the multiple analyte assay is capable of detecting less than 2.5 copies of more than one different target nucleic acid bearing a given nucleic acid sequence.

EXAMPLE 10

Polymerase Chain Reaction (PCR)

PCR is a nucleic acid amplification technique well known to and regularly employed by those of ordinary skill in the art (see e.g., American Society for Microbiology, Diagnostic Molecular Microbiology: Principles and Applications 56–70 (1993), incorporated by reference herein), and is patented technology owned and licensed by Hoffman-LaRoche, Inc., Nutley, N.J.

A general procedure for PCR amplification of nucleic acids is taught in Sambrook et al., supra at page 14.18 (incorporated by reference herein). In the procedure so provided, the following ingredients are mixed in a sterile 0.5 ml microcentrifuge tube for each reaction: 30 μl of sterile water, 10 μl of a 10X Amplification buffer (10X Amplification buffer=500 mM KCL, 100 mM Tris-Cl (pH 8.3), 15 mM MgCl and 0.1% (w/v) gelatin), 1.25 mM each dNTP, 100 pmoles of each primer, up to 2 μg of template DNA, and water to a final volume of 100 μl. The reaction mixture is heated at 94° C. for 5 minutes. 5 μl of a 5 unit/μl preparation of Taq DNA polymerase (Perkin-Elmer Corporation, Norwalk, Conn.) is added to the reaction mixture. The reaction mixture is then given 100 μl of light mineral oil and the reaction mixture incubated for 5 minutes at 94° C. to denature hydrogen-bonded nucleic acids, then for 2 minutes at 50° C. to allow annealing of the primers to the single-stranded target nucleic acids and 3 minutes at 72° C. to allow primer extension. The reaction mixture is then sequentially incubated for 1 minute at 94° C., 2 minutes at 50° C. and 3 minutes at 72° C., in that order, through 20 cycles. The sample is incubated at 72° C. for 10 minutes in the last step of the last cycle, then stored at −20° C. for use.

EXAMPLE 11

Detection of the gag and pol Regions of HIV DNA Following PCR Amplification

The method of the present invention was used to simultaneously detect the presence of both the gag and pol regions of HIV DNA. In this experiment the viral DNA was amplified using the polymerase chain reaction (PCR) prior to detection.

The probes used were the same as used in Example 8. HIV-1 DNA was amplified using PCR; the primer pairs used to amplify the pol region by PCR had nucleotide sequences of SEQ ID NOs: 2 and 4, and the primers used to amplify the gag region had nucleotide sequences SEQ ID NOs: 7 and 10.

After amplification, nucleic acid hybridization was carried out by mixing 20 μl of the PCR reaction mixture with 80 μl of water, and then adding 100 μl of the probe mixture described in Example 8. The probe and target nucleic acids were incubated together for 30 minutes at 60° C. Differential hydrolysis, measurement of the chemiluminescence, and calculation of the results were performed as described in Example 8. The assay results are shown in Table 11 below.

TABLE 11

| Input Template Nucleic Acid Sequence (before amplification) (Average # Copies) | Total Observed RLU | Calculated Values (RLU) | |
|---|---|---|---|
| | | pol | gag |
| 25 | 173882 | 92838 | 65793 |
| 25 | 97173 | 53868 | 35657 |
| 10 | 107820 | 51472 | 44106 |
| 10 | 67621 | 35681 | 21349 |
| 2.5 | 65989 | 31730 | 27207 |
| 2.5 | 38210 | 18367 | 15040 |
| 0 | 975 | 101 | 732 |
| 0 | 286 | 75 | 56 |

These data demonstrate that the multiple analyte assay method of the present invention can simultaneously detect the presence of different nucleic acid molecules having sequences corresponding to the gag and pol regions of HIV-1 when the HIV-1 sequences have been amplified using the polymerase chain reaction.

EXAMPLE 12

Simultaneous Detection of More Than Two Analytes in a Single Test Sample

As an illustration of the feasibility of detecting more than two analytes in a single sample the following experiments were performed.

The following AE derivatives were individually coupled to separate oligonucleotide probes as disclosed above: diBr-AE; 2,7,-diMe-AE; o-MeO-(cinnamyl)-AE, o-Me-AE, and o-diMe-AE. Approximately 0.003 pmoles of each indicated coupled chemiluminescent label in a volume of 1.5 μl per label were added to a tube as shown in Table 12 below, then given 200 μl of a solution containing 0.4N HCl, 0.1% $H_2O_2$. Each tube was loaded into a LEADER® 50 luminometer, given an automatic injection of 1N NaOH, and the resulting emitted light measured over a period of 10 seconds in intervals of 0.1 second.

TABLE 12

| Tube | AE-Derivatives |
| --- | --- |
| 1 | o-diBr—AE and 2,7-diMe—AE |
| 2 | Same as 1 plus o-MeO(cinnamyl)—AE |
| 3 | Same as 2 plus o-Me—AE |
| 4 | Same as 3 plus o-diMe—AE |

Figure 4:
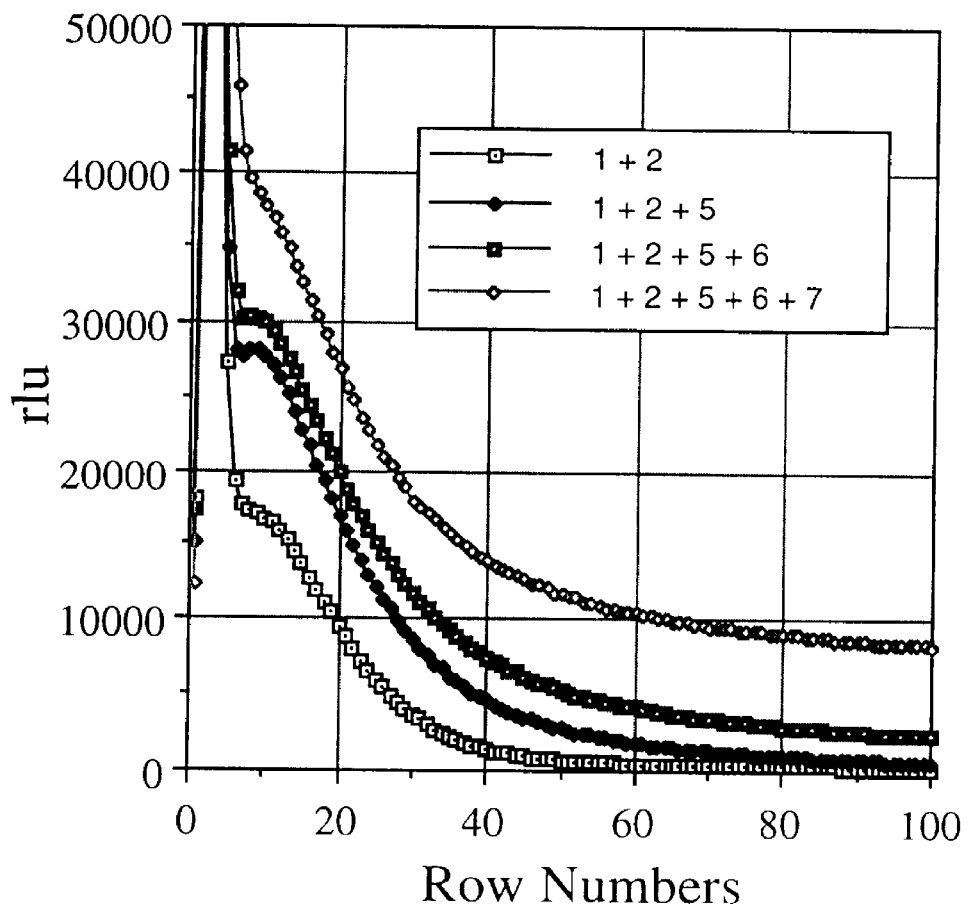
FIG. 4 is a graphic display of the overlapping characteristic light emission profiles from five different combinations of chemiluminescent labeling reagents over time. A triggering reagent was added to each reaction mixture at time zero. The labeling reagents used in this figure were: o-diBr-AE, 2, 7-diMe-AE, o-MeO (cinnamyl)-AE, o-Me-AE and o-diMe-AE.

Plots showing the resulting light emission profiles obtained from of these experiments are shown in FIG. 4. The units of the x-axis are given in interval number, and the units of the y-axis are given in RLU; the emission profiles are displayed in a single overlay plot. This plot clearly shows that the decay of each reacting chemiluminescent compound in the samples is sufficiently different from each other reacting chemiluminescent compound that each compound can be distinguished from the others. For example, the light emission from Tube 1 (o-diBr-AE and 2,7-diMe-AE) reaches baseline at approximately interval 50 (5.0 seconds). Thus, the light emitted in intervals 46–100 can be assumed to be the sum of that emitted by Tubes 2, 3 and 4. (Tube 1 contained both o-diBr-AE and 2,7-diMe-AE; it will be appreciated by one of skill in the art that o-diBr-AE can be clearly distinguished from the other AE derivatives used in this experiment, and from 2,7-diMe-AE in particular, in a mixture containing all these compounds, since its light emission reaches baseline at approximately interval 10). Likewise, the light emitted by the chemiluminescent compounds contained in Tube 2 (o-diBr-AE, 2,7-diMe-AE and o-MeO(cinnamyl)-AE) reaches baseline at about interval 80 (8.0 seconds); the light emitted in intervals 69–100 can be assumed to be the sum of the light emitted by the chemiluminescent compounds contained in Tubes 3 and 4. Finally, the light emitted by the compounds in Tube 3 (o-diBr-AE, 2,7-diMe-AE, o-MeO(cinnamyl)-AE and o-Me-AE) reaches baseline at some point after interval 100. Although not shown in the Figure, at this latter time the components of tube 4 are still emitting measurable light.

Thus, by selecting the time periods during which to measure the light emitted by the compounds in each tube, one can distinguish between the light emitted by each compound using a reiterative averaging process similar to that used in Example 3 above to distinguish two chemiluminescent labels. Using the disclosure of the present example as a guide, it would be reasonably expected by those of skill in the art that o-diBr-AE, 2,7-diMe-AE, o-MeO(cinnamyl)-AE, o-Me-AE, and o-diMe-AE coupled to oligonucleotide probes can be distinguished under these reaction conditions. Moreover, it would also be reasonably expected by those of skill in the art that this ability would not be defeated when the probes are hybridized to a target nucleic acid.

EXAMPLE 13

Figure 5:
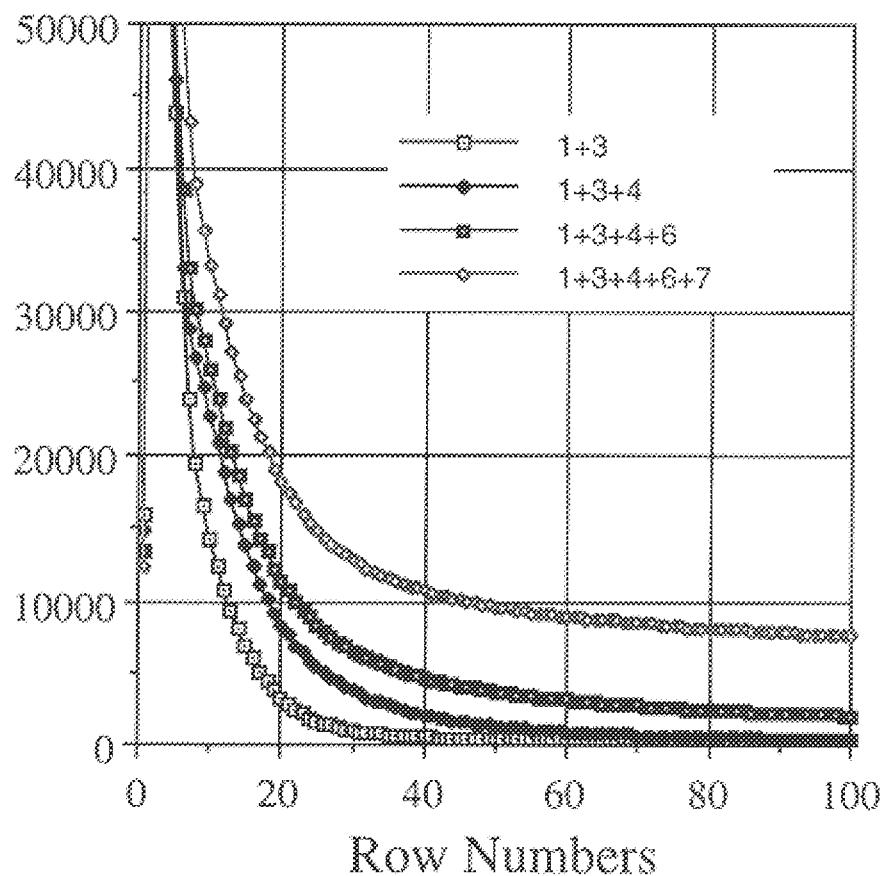
FIG. 5 is a graphic display of the overlapping characteristic light emission profiles from five different combinations of chemiluminescent labeling reagents over time. A triggering reagent was added to each reaction mixture at time zero. The labeling reagents used in this figure were: o-diBr-AE, a mixture of 1- and 3-Me-AE, o-AE, o-Me-AE and o-diMe-AE.

Evaluation of Additional Chemiluminescent Reagents for Use in a Multiple Analyte Assay The evaluation of the following probe-coupled chemiluminescent reagents was performed as described in the previous example, except emitted light was measured for a total of 10 seconds at time intervals of 0.1 second, and each chemiluminescent reagent was evaluated separately rather than in a mixture as in Example 12. FIG. 5 shows a overlay plot of the separately assayed light emissions of 1) a combination of o-diBr-AE and a mixture of 1- and 3-Me-AE, 2) the same as 1), plus ortho-AE, 3) the same as 2), plus o-Me-AE, and 4) the same as 3), plus o-diMe-AE. As can be seen from the plot, the o-diBr-AE/1- and 3-Me-AE mixture reacts quickly and emits little light after approximately interval 40, at which time the other AE derivatives still emit light. The ortho-AE emits little light after about interval 80. Although this Figure does not show the baseline resolution of the o-Me-AE derivative, additional experimentation has confirmed that the light emission decay of this derivative consistantly proceeds more quickly than does the reaction of the remaining AE-derivative, o-diMe-AE. Extrapolation of the curves for these latter two compounds indicates that the kinetic profiles of these derivatives would be distinguishable in later time intervals than are shown in this Figure.

Although the coupled o-diBr-AE and 1- and 3-Me-AE labels were combined in this experiment, it has already been demonstrated that o-diBr-AE and a mixture of 1- and 3-Me-AE can be distinguished on the basis of their characteristic reaction kinetics, (see e.g., Example 3).

These data indicate that, using the same reiterative averaging method used in Example 3 above to distinguish two chemiluminescent labels, the signals for each member compound in this set of coupled chemiluminescent labels are capable of being distinguished in a single sample when a light-emitting reaction involving all the member compounds is simultaneously initiated, and the emitted light is detected over an appropriate period of time.

EXAMPLE 14

Evaluation of Seven Chemiluminescent Labels for Simultaneous Use in a Multiple Analyte Assay The reaction kinetics of seven different chemiluminescent labels (o-diBr-AE, 2,7-diMe-AE, a mixture of 1- and 3-Me-AE, o-linker-AE, o-MeO(cinnamyl)-AE, o-Me-AE, and o-diMe-AE) were evaluated by separately measuring the light emitted by each compound following initiation of a chemiluminescent reaction. Each chemiluminescent label was coupled to a different oligonucleotide. The experimental conditions were the same as in Example 12 except as indicated herein. Emitted light was measured over a total time of seven seconds at 0.1 second intervals, and detected and measured using a luminometer.

Figure 6:
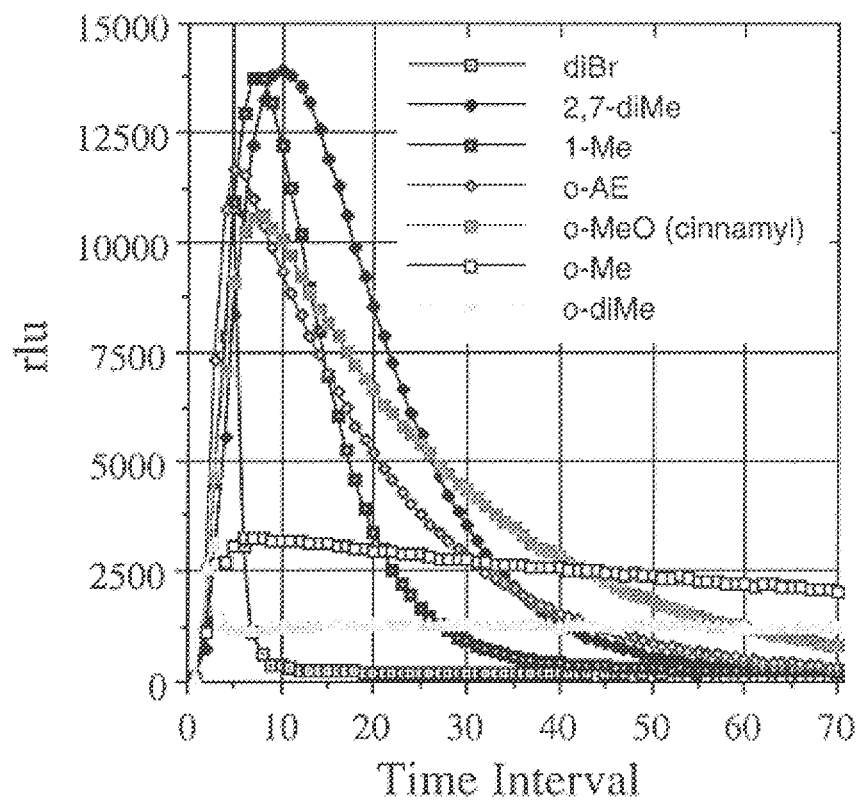
FIG. 6 is a graphic display of the overlapping characteristic light emission profiles from seven different chemiluminescent labeling reagents over time. A triggering reagent was added to each reaction mixture at time zero. The labeling reagents used in this figure were: o-diBr-AE, 2, 7-diMe-AE, a mixture of 1- and 3-Me-AE, o-AE, o-MeO (cinnamyl)-AE, o-Me-AE and o-diMe-AE.

FIG. 6 shows the resulting light emission characteristics of these compounds as a computer-generated single plot comprising the superimposed individual plots for each chemiluminescent compound. As this Figure clearly shows, the decay of emitted light by each reacting compound is sufficiently different and distinct from that of each other chemiluminescent compound that each may be separately detected and measured in a single test sample when reaction is initiated simultaneously. It will be appreciated by those of skill in the art in light of the present disclosure that while this example presents data gathered separately for each member compound, the reaction kinetics and decay of emitted light would not differ substantially when these compounds are combined in a single sample. Thus, the person of skill in the art would realize that the present example provides a set of seven chemiluminescent reagents which may be used simultaneously in a single assay for the detection of seven nucleic acid analytes in accordance with the compositions and methods of the present invention.

EXAMPLE 15

Evaluation of Chemilumunescent Reagents for Multiple Mode, Multiple Analyte Assay System The following chemilumunescent reagents were evaluated for use in a four analyte, two-pH assay system: o-diBr- AE, o-F-AE, standard AE, and o-MeO(cinnamyl)-AE. As in the previous example, each chemiluminescent reagent was coupled to a different oligonucleotide. Experimental conditions were the same as in Example 4 except the oligonucleotides were given 74 $\mu$l 0.4N HCl+26 $\mu$l $H_2O$ prior to addition of $H_2O_2$. Each chemiluminescent reagent was evaluated separately.

Figure 7:
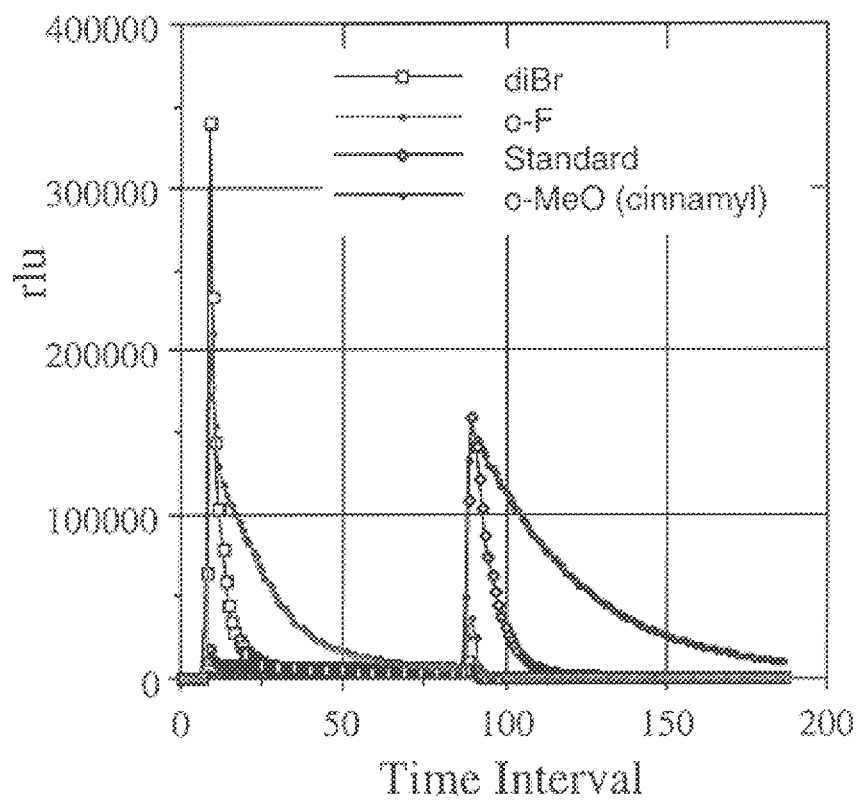
FIG. 7 shows the superimposed characteristic light emission profiles of four chemiluminescent labeling reagents in a multiple pH assay mode over time. The figure demonstrates the ability of the present assay to detect four analytes in a multiple mode assay system.

FIG. 7 shows the results of each experiment combined in a computer generated single plot wherein the data obtained for each chemiluminescent reaction is superimposed for greater clarity. As can be seen, the o-diBr-AE and o-F-AE participate in a chemiluminescent reaction at the first pH. Moreover, these two reagents are clearly distinguishable from each other with the light emitted by the o-diBr-AE having decayed to baseline at approximately interval 25. The light emitted between intervals 25 and 75 represents the contribution of the o-F-AE reagent. It can also be seen that standard AE and o-MeO(cinnamyl)-AE are relatively resistant to reaction at this pH, with only a small amount of light emitted by each compound between intervals 0 and approximately 85.

The pH of the reaction mixtures was adjusted to 13 at a time corresponding to approximately interval 85. As can be seen, this pH shift allowed the largely unreacted standard AE and o-MeO(cinnamyl)-AE to emit light at a time when virtually all of the o-diBr and o-F-AE derivatives had already reacted at the previous pH. The two reagents reacting at the new pH value can also be clearly distinguished on the basis of the time required for each compound to completely react; standard AE has almost completely reacted by interval 120, while o-MeO(cinnamyl)-AE is still emitting light between intervals 120 and approximately 175.

This example demonstrates the versatility of the compositions and methods of the present invention. As demonstrated herein, more than one mode of the present invention may be combined to allow the detection of two or more nucleic acid analytes. It will be clear to one of skill in the art that although the data presented herein was gathered from compounds evaluated in separate reaction mixtures, these compounds would be reasonably expected to have substantially similar reaction characteristics when combined in a single reaction mixture; see, e.g., Example 16. Such a person would also understand that the reaction characteristics of these compounds would not be materially altered when the oligonucleotide to which they are coupled is hybridized to a complementary nucleic acid strand.

EXAMPLE 16

Correlation between Predicted and Actual Reaction Characteristics of Combined Chemiluminescent Reagents In order to demonstrate that the reaction characteristics of the preferred acridinium ester derivatives exemplified in the previous examples are accurately predicted by a computer-generated superimposition of plots obtained from individually assayed chemiluminescent reagents, the following experiment was performed. Individual reaction mixtures were made according to the protocol of Example 15. Each tube contained one of the following acridinium esters: o-diBr-AE, o-F-AE, standard AE, and o-MeO(cinnamyl)-AE. In addition, individual tubes were made using the same amounts of each compound combined in a single tube as follows: o-diBr and o-F-AE, standard AE and o-MeO-AE, and o-diBr-AE, o-F-AE, standard AE, and o-MeO-AE. All of the chemilumunescent reagents were coupled to separate oligonucleotides, as in the previous examples. Reaction was initiated and measured as in Example 15. The results are shown in FIG. 8(A–I).

Figure 8A:
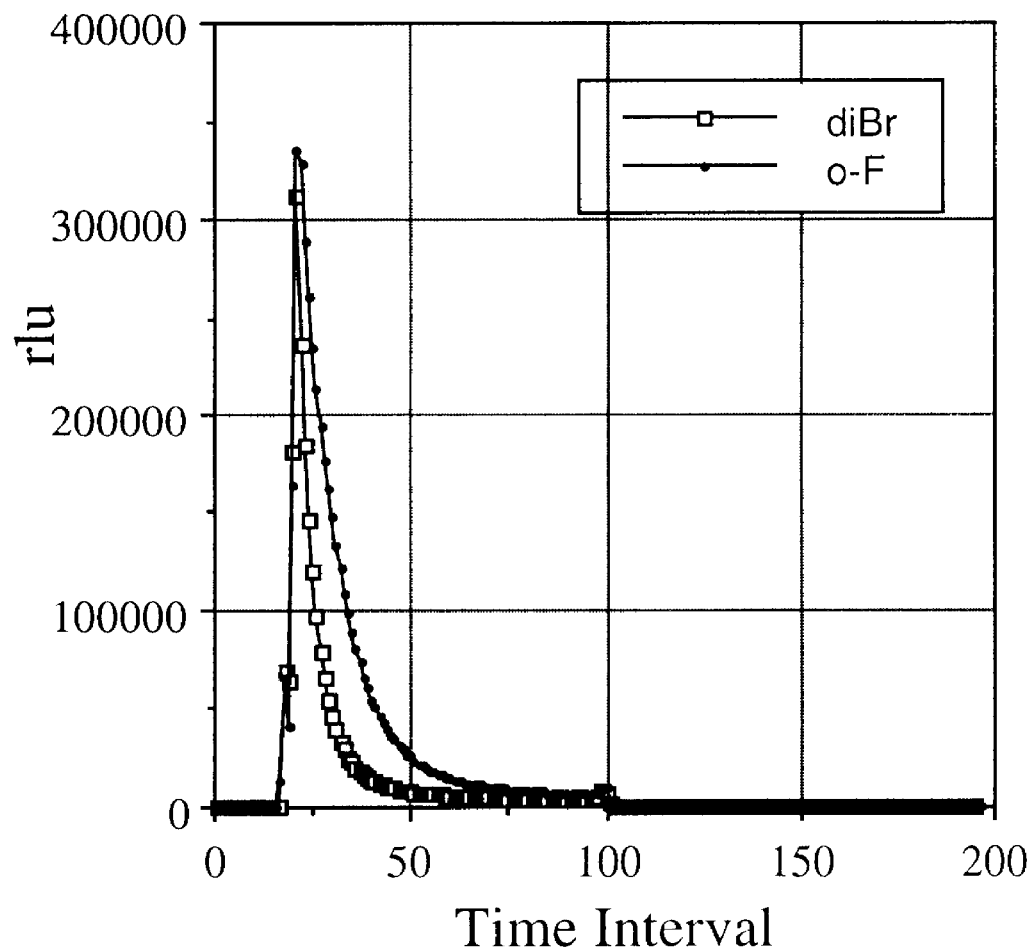
FIGS. 8A through 8I graphically demonstrate the correlation between the expected light emission profiles of combined chemiluminescent labeling reagents versus the actual light emission profiles obtained. The chemiluminescent labeling reagents used were: o-diBr-AE, o-F-AE, standard AE and o-MeO-AE. The chemiluminescent reactions were conducted in a multiple pH assay system under identical conditions.
Figure 8B:
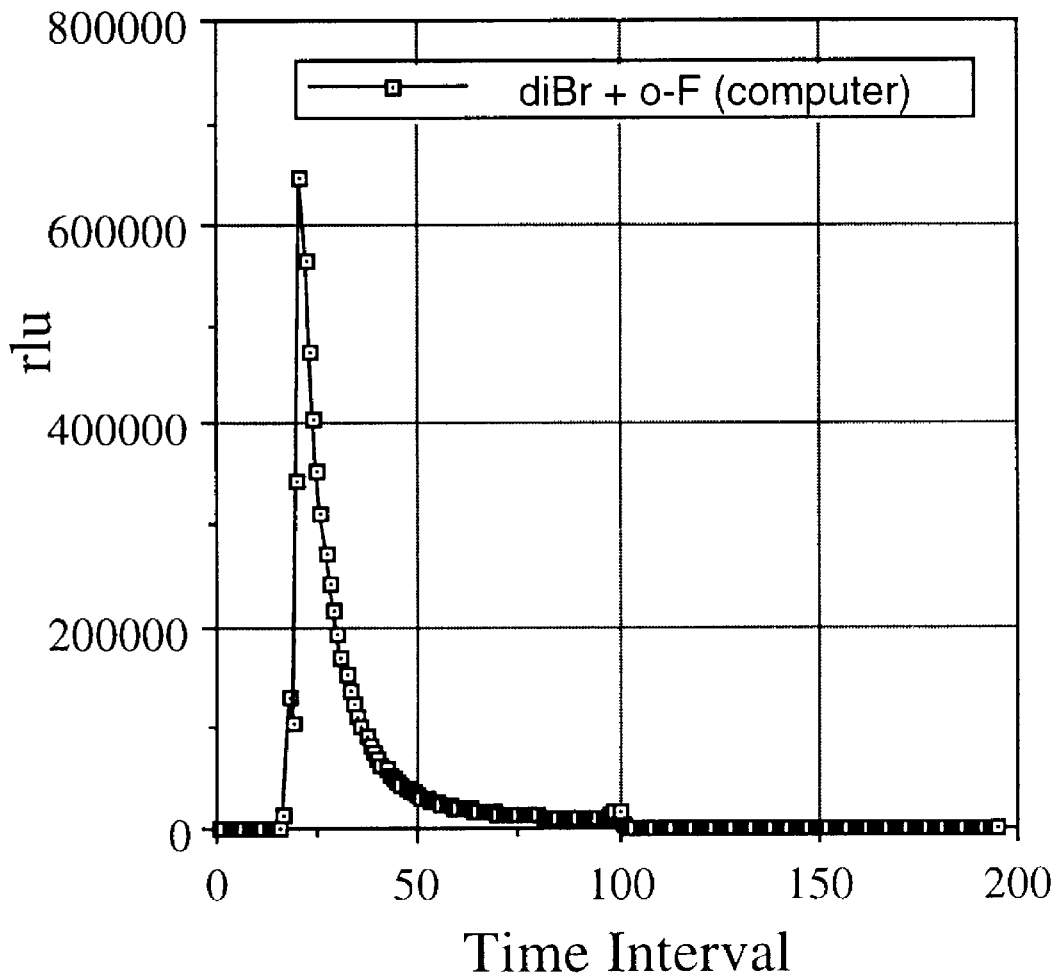
Figure 8C:
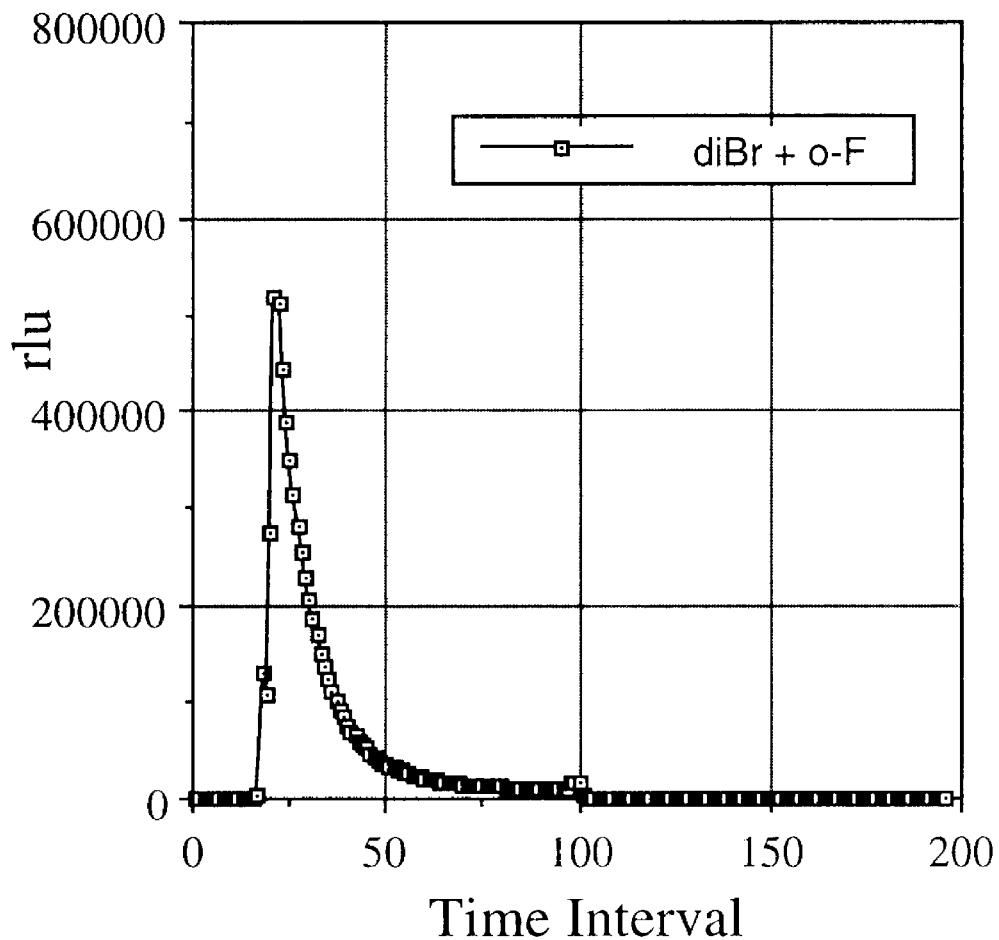

FIG. 8A shows a computer-generated superimposed plot of the light emitted by o-diBr-AE and o-F-AE which had been separately assayed. FIG. 8B shows a computer-generated plot of the combined light emitted by both reagents; this plot is the sum of the individual plots of FIG. 8A, and represents a prediction of the reaction characteristics of a single reaction mixture containing both reagents. FIG. 8C shows the actual reaction characteristics of a mixture of these two compounds in a single tube. These data clearly demonstrate that not only is the decay of light emission the same for FIG. 8B (predicted curve) and FIG. 8C (actual curve), but the kinetic curves are substantially identical.

Figure 8D:
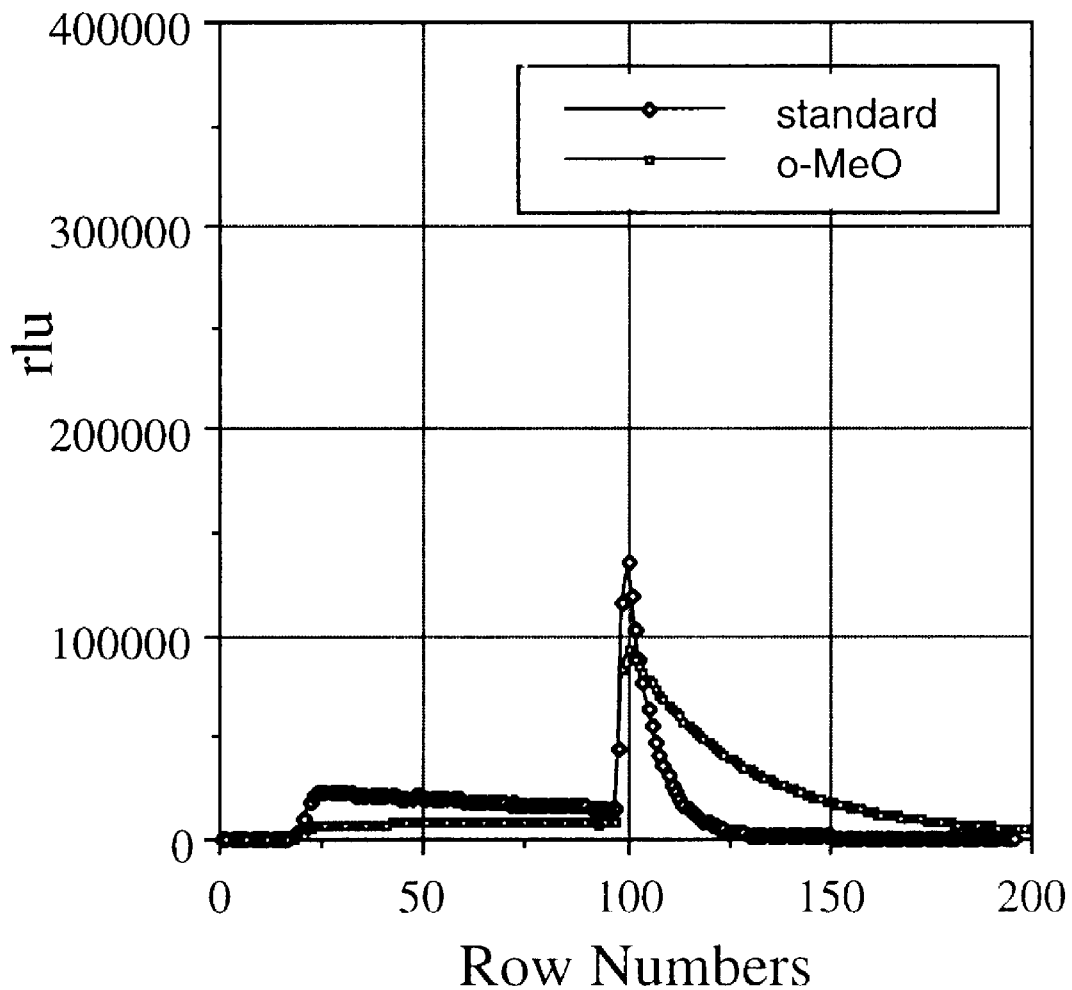
Figure 8E:
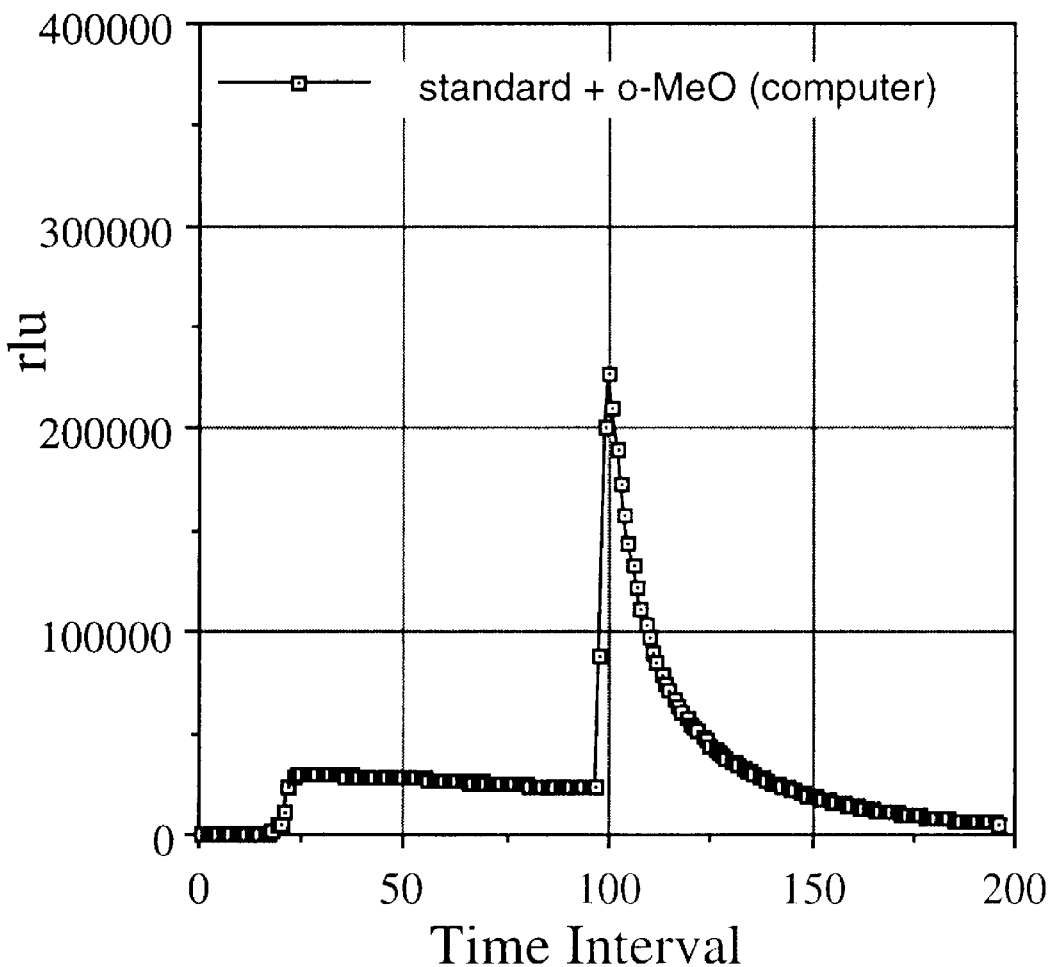
Figure 8F:
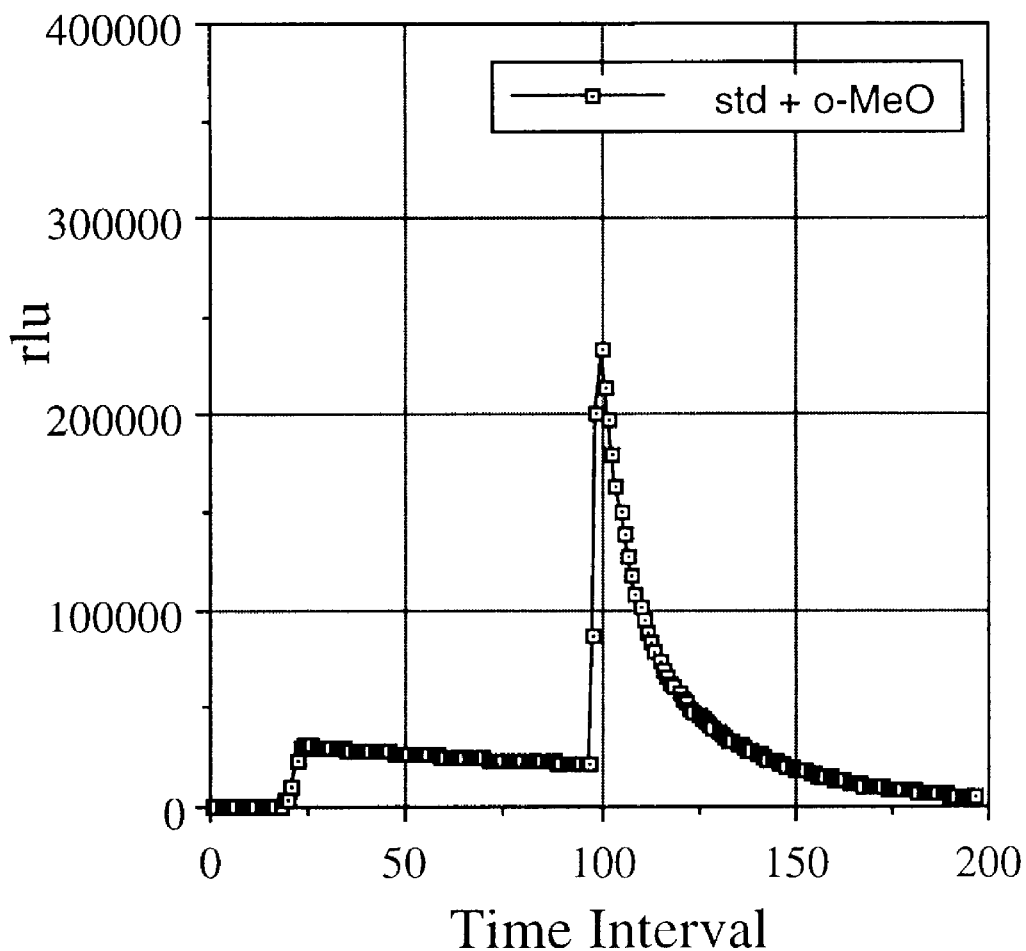

FIG. 8D similarly shows a computer-generated superimposed plot of the light emitted by standard AE and o-MeO (cinnamyl)-AE which had been separately assayed. FIG. 8E displays the computer-generated sum of these superimposed plots, and FIG. 8F shows the actual light emitted by a mixture of these two compounds following initiation of a chemiluminescent reaction. A comparison between FIGS. E and F shows that the reaction characteristics of a mixture of standard AE and o-MeO(cinnamyl)-AE are accurately predicted by adding the curves obtained from the two individually assayed AE derivatives.

Figure 8G:
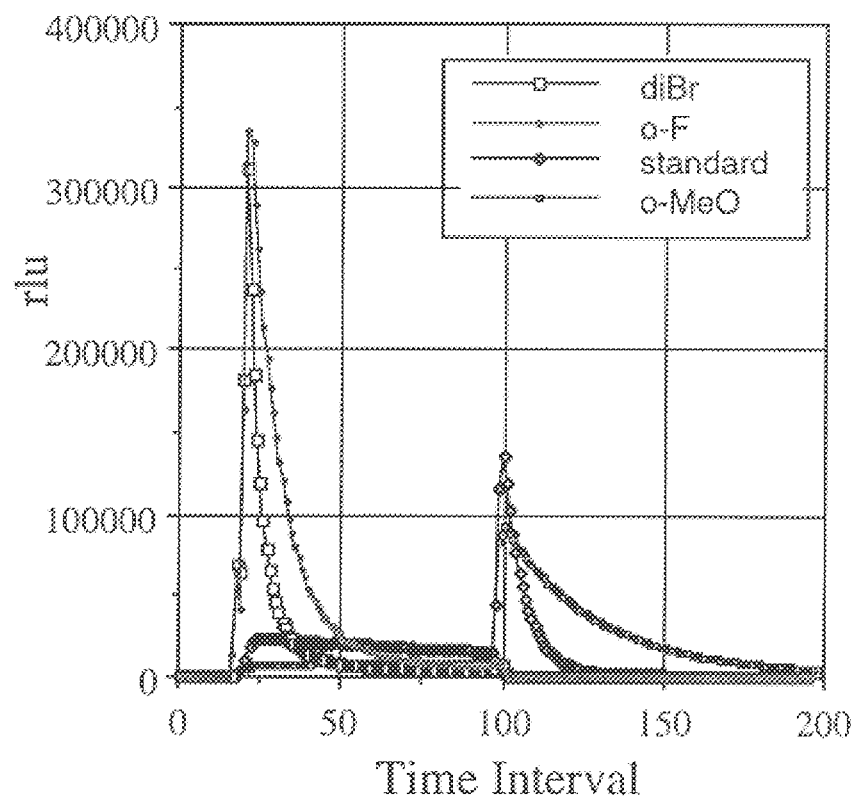
Figure 8H:
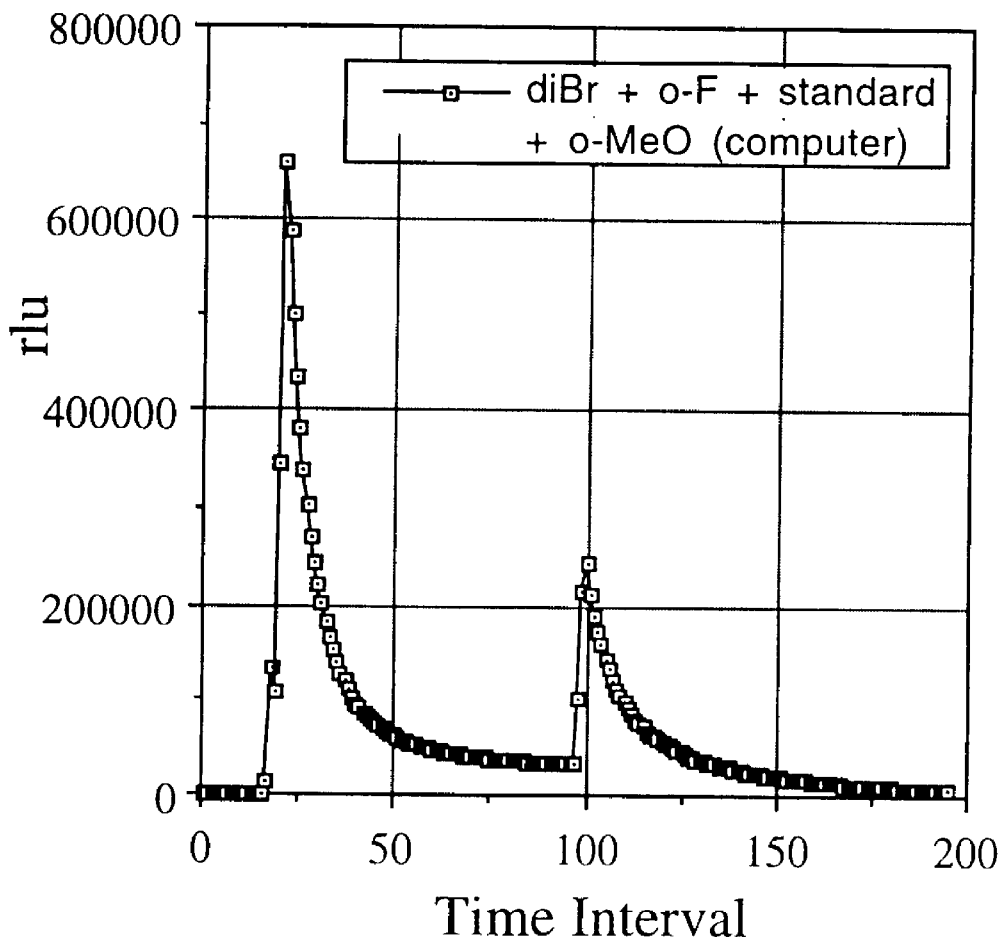
Figure 8I:
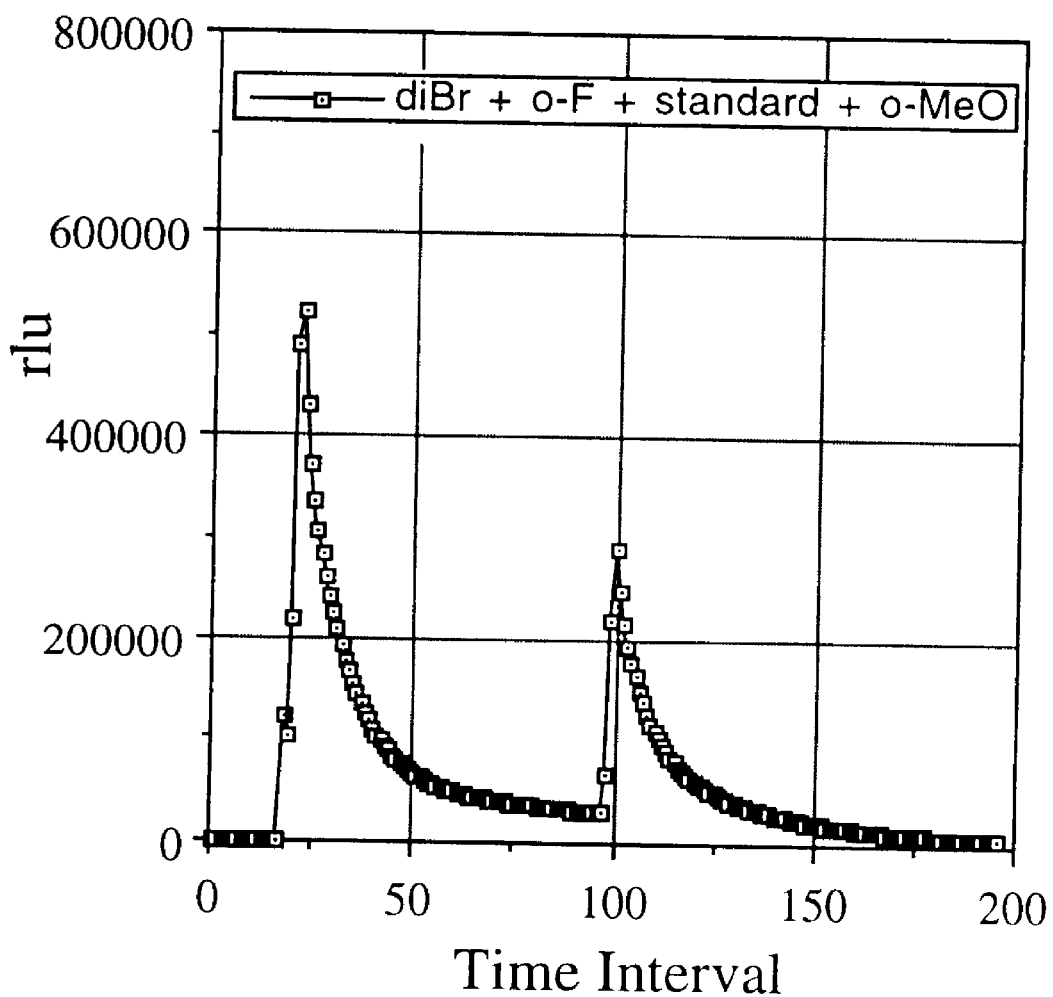

Finally, FIG. 8G shows superimposed plots of the light emitted by all four of these individually assayed acridinium ester derivatives. FIG. 8H is a computer-generated sum of the plots of FIG. 8G, and FIG. 8I shows the light emission characteristics of a mixture of all four of these compounds over time. Thus, FIG. 8H shows the predicted light emission characteristics of the four compounds and FIG. 8I, the actual results. Again, there is close to an exact correlation between the "predicted" plot of FIG. 8H and the "actual" plot of FIG. 8I.

This experiment demonstrates that the characteristic reaction kinetics of each AE label is not significantly different when they are mixed with other AE labels in a single reaction mixture. Thus, the AE labels disclosed for use in the methods and compositions of the present invention and are demonstrably suitable in a multiple analyte assay system.

EXAMPLE 17

Mode Three: Multiple Wavelengths, Simultaneous Initiation

In an additional embodiment of the present invention, multiple analytes may be simultaneously detected in a single sample by using different oligonucleotide probes each labeled with a different chemiluminescent label which emits light at a different wavelength than each other label.

As an example of this mode of the invention, the assay could be run essentially as in Example 6, with the following modifications. After the hybridization, each tube is given 1 ml of a solution of 60 mM sodium tetraborate (pH 8.9), 6.89% (v/v) TRITON® X-102 detergent and 0.1% (w/v) gelatin containing 50 $\mu$l of a 1.25% (w/v) suspension of BIOMAG™ 4100 magnetic particles in 0.02% (w/v) sodium azide and 1 mM EDTA. Incubation and wash steps are as in Example 6.

Figure 9A:
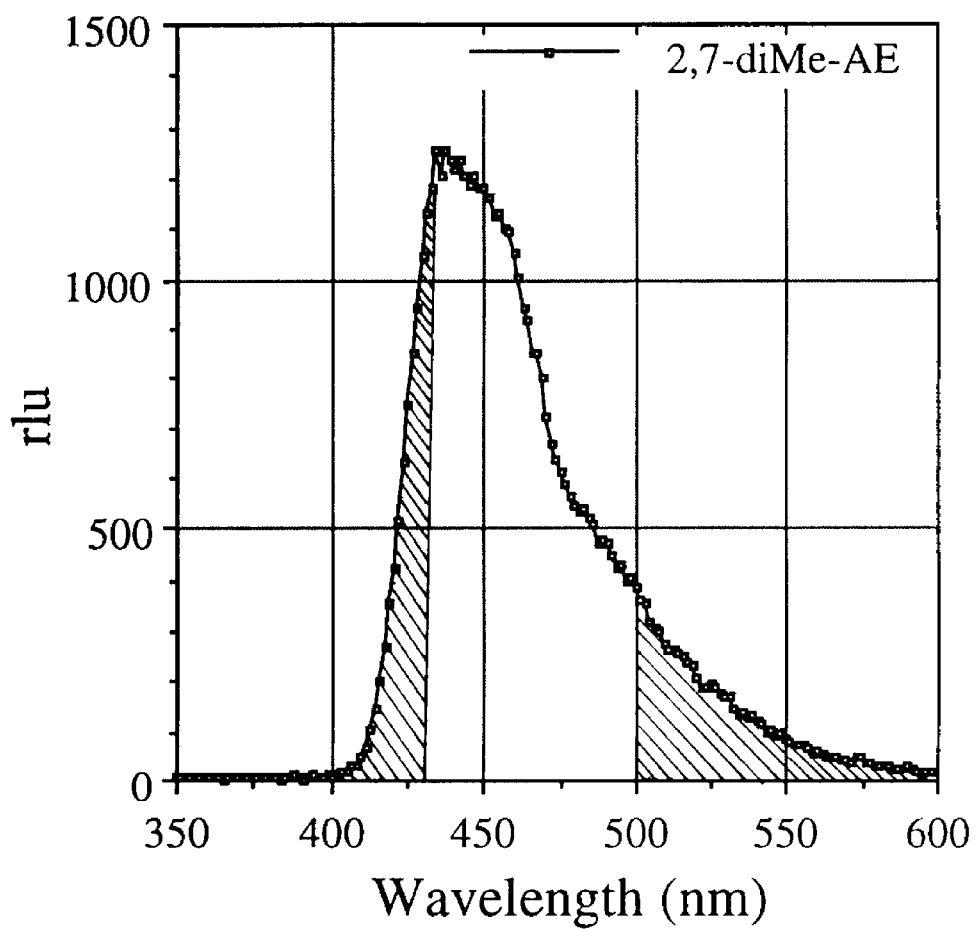
FIGS. 9A through 9D are chemiluminescent spectra of two acridinium ester derivatives.
Figure 9B:
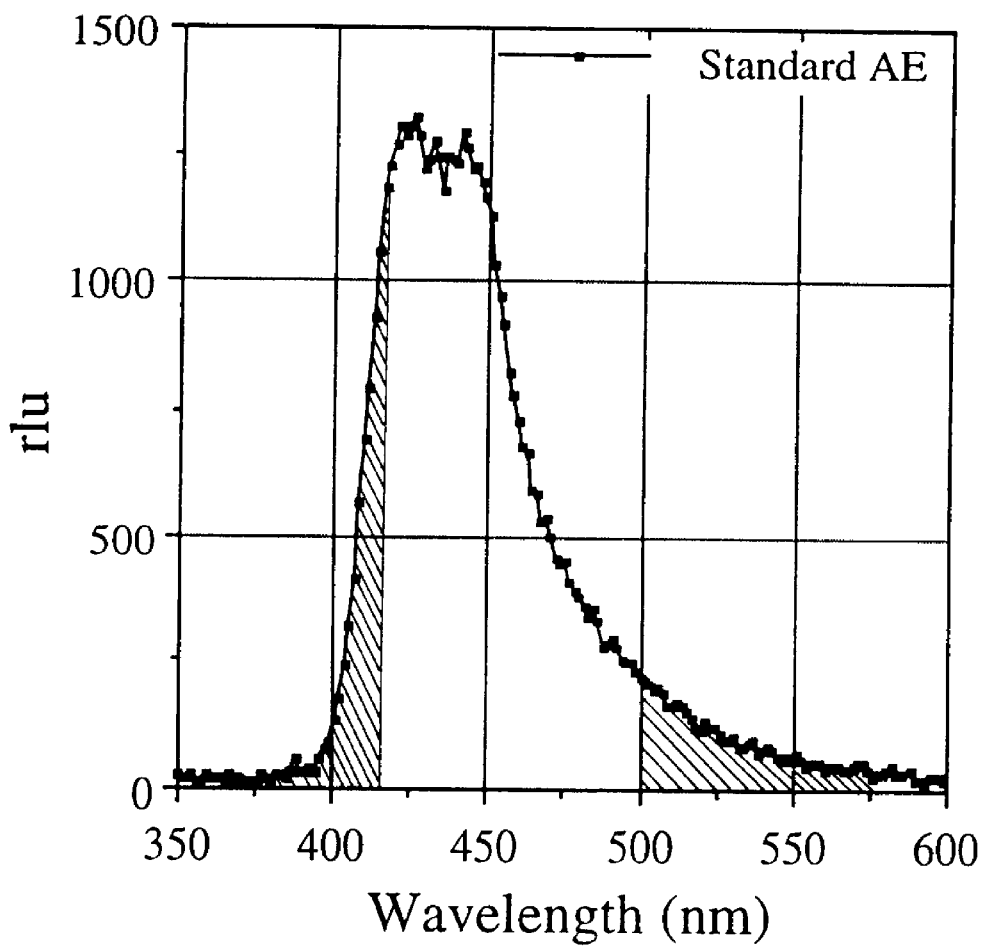
Figure 9C:
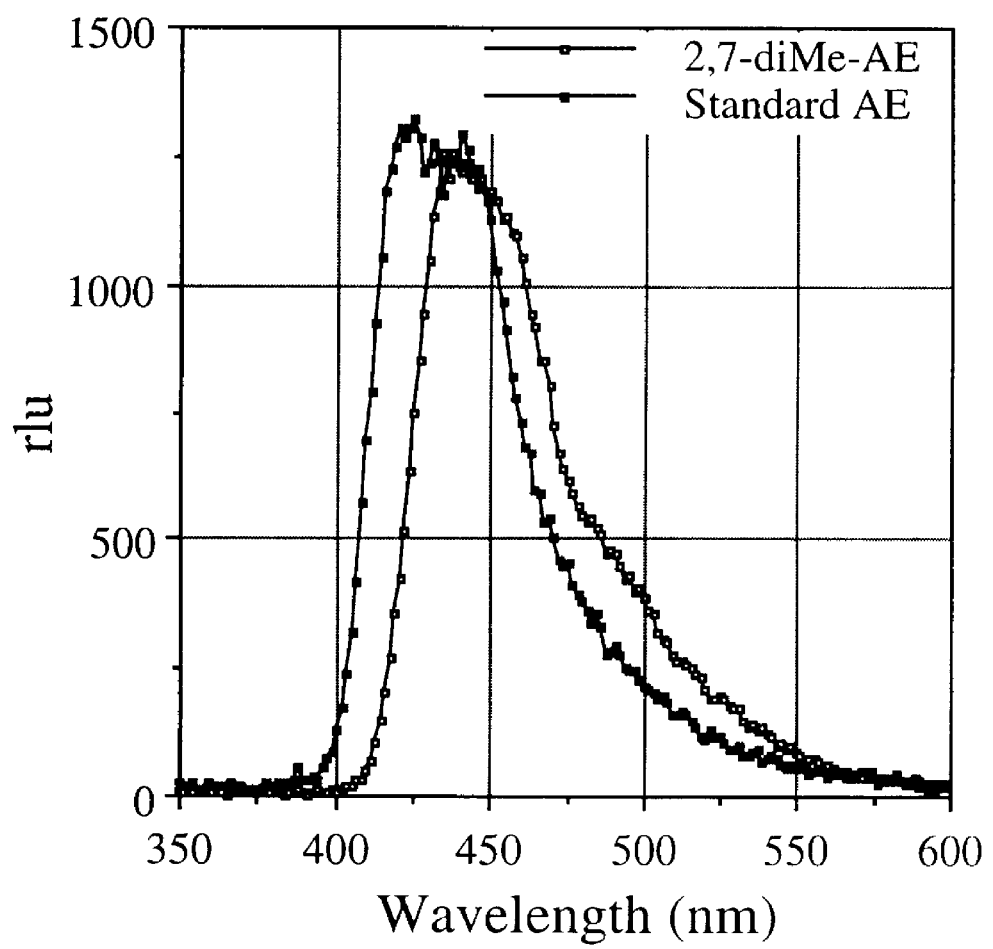
Figure 9D:
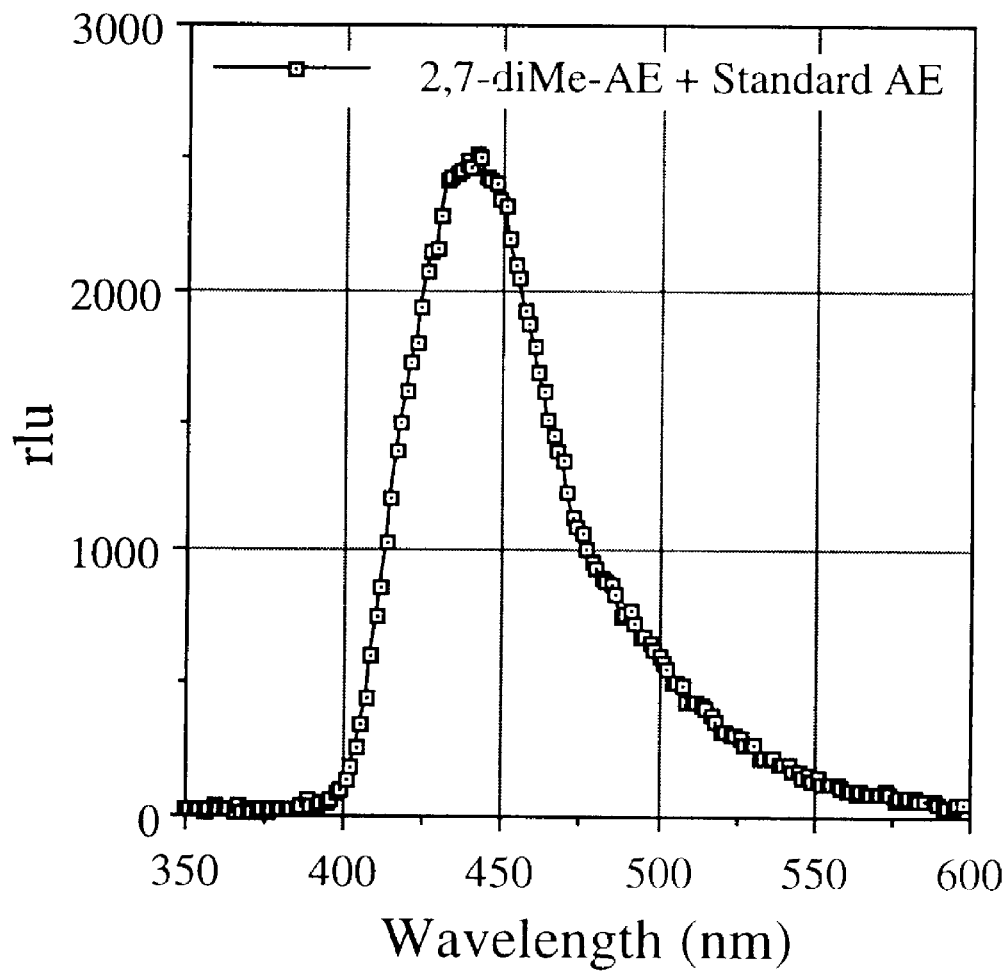

A luminometer is equipped with 4 photomultiplier tubes (PMT's), one monitoring emitted light in the wavelength range from 300 nm to 700 nm, one having a 375 to 415 nm cut-off filter, one having a 400 nm to 435 nm cut-off filter, and one having a 500 nm to 575 nm cut-off filter. Standards of each label are loaded into the luminometer, caused to emit light, and the emitted light monitored by each PMT. Ratios of the chemiluminescence in each wavelength window are determined for each label as illustrated in the calculation method of Example 3. FIGS. 9A and 9B show the chemiluminescent spectra of 2,7-diMe-AE and standard AE; the shaded portions of these spectra represent the wavelength windows referred to above. FIG. 9C is a computer-generated overlay of the spectra of 9A and 9B. As can be seen, the maximum wavelength emission is different for each label, and each label may be distinguished in a mixture of the two. FIG. 9D is a computer-generated sum of the two individual wavelength emission profiles.

Having determined the standard ratios of wavelength emission for the specific chemiluminescent labels to be used, each experimental sample is loaded into the luminometer, a light emitting reaction is initiated, and the resulting emitted light is monitored in exactly the same way as for the standards. Results can then be determined using the reiterative calculation method of Example 3.

The foregoing examples are intended to be illustrative only, and in no way are intended by the Applicant to limit the scope of the present invention. Additional embodiments are given in the following claims.

What is claimed is:

1. A composition which can be used to assay for the presence of a plurality of nucleic acid analytes which may be present in a sample comprising:
   a) a plurality of different oligonucleotide probes, each of said probes having a nucleotide sequence which binds to a target nucleotide sequence of at least one nucleic acid analyte under selective conditions,
   wherein each of said probes binds to a different target nucleotide sequence under said conditions, and
   wherein said probes do not bind to non-targeted nucleic acids present in said sample under said conditions; and
   b) a plurality of different chemiluminescent labels, each of said labels being capable of emitting light at one or more different wavelengths when a light-emitting reaction is initiated, and each of said labels being coupled to at least one of said probes, said probes collectively targeting at least two nucleic acid analytes which may be present in said sample,
   wherein the chemiluminescent potential of said labels is susceptible to selective alteration when said labels are not associated with a probe:analyte hybrid,
   wherein the rate at which each of said labels associated with a probe:analyte hybrid is altered is less than about 50-fold different than the rate at which any other of said labels associated with a probe:analyte hybrid is altered, and
   wherein the rate at which each of said labels not associated with a probe:analyte hybrid is altered is less than about 50-fold different than the rate at which any other of said labels not associated with a probe:analyte hybrid is altered, and
   wherein said light emitting reaction causes each of said labels associated with a probe:analyte hybrid to emit light at one or more wavelengths sufficiently distinct from the one or more wavelengths of light emitted by any other of said labels associated with a probe:analyte hybrid, such that each of said labels associated with a probe:analyte hybrid is independently and selectively detectable when the emitted light is simultaneously detected at said one or more wavelengths, thereby indicating presence of one or more of said nucleic acid analytes which may be present in said sample.

2. The composition of claim 1 wherein at least two of said labeled probes will specifically hybridize with *Chlamydia trachomatis* and *Neisseria gonorhoeae* nucleic acids, respectively.

3. The composition of claim 1 wherein at least two of said labeled probes will each specifically hybridize with different nucleic acid analytes contained in the same nucleic acid.

4. The composition of claim 1 in which at least one of said chemiluminescent labels is an acridinium ester derivative.

5. The composition of claim 4 in which said acridinium ester is selected from the group consisting of:
   a) standard AE
   b) naphthyl AE
   c) o-diBr AE
   d) 1- and 3-Me AE
   e) 4,5-diMe AE
   f) 2,7-diMe AE
   g) o-Me AE
   h) o-MeO(cinnamyl) AE
   I) o-MeO AE
   j) ortho AE
   k) o-F-AE
   l) 1 and 3-Me-o-F AE
   m) 2,7-diMe-o-F AE, and
   n) 1- and 3-Me-m-diF AE.

6. The composition of claim 5 in which at least two said chemiluminescent labels are acridinium esters.

7. The composition of claim 6 in which one of said acridinium esters is selected from the group:
   a) standard AE,
   b) naphthyl AE,
   c) o-diBr AE,
   d) 1- and 3-Me AE,
   e) 4,5-diMe AE,
   f) 2,7-diMe AE,
   g) o-Me AE,
   h) o-MeO(cinnamyl) AE,
   I) o-MeO AE,
   j) ortho AE,
   k) o-F-AE,
   l) 1 and 3-Me-o-F AE,
   m) 2,7-diMe-o-F AE, and
   n) 1- and 3-Me-m-diF AE.

8. The composition of claim 7 wherein a first acridinium ester is standard AE and a second acridinium ester is 2,7-diMe AE.

9. The composition of claim 1 in which all said chemiluminescent labels are different acridinium ester derivatives.

* * * * *